United States Patent
Leeson et al.

(10) Patent No.: US 10,470,853 B2
(45) Date of Patent: Nov. 12, 2019

(54) CONTINUOUS CUSTOM DENTAL RESTORATION MANUFACTURING PROCESS AND SYSTEM

(71) Applicant: James R. Glidewell Dental Ceramics, Inc., Newport Beach, CA (US)

(72) Inventors: David Christopher Leeson, North Tustin, CA (US); James Fidel Zamora, Eastvale, CA (US); Dong Hee Phee, Diamond Bar, CA (US); Nicolas Ziegler, Costa Mesa, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 304 days.

(21) Appl. No.: 15/368,122

(22) Filed: Dec. 2, 2016

(65) Prior Publication Data

US 2017/0156828 A1   Jun. 8, 2017

Related U.S. Application Data

(60) Provisional application No. 62/262,616, filed on Dec. 3, 2015.

(51) Int. Cl.
*A61C 13/00* (2006.01)
*B23Q 3/06* (2006.01)

(52) U.S. Cl.
CPC ...... *A61C 13/0006* (2013.01); *A61C 13/0004* (2013.01); *A61C 13/0022* (2013.01); *B23Q 3/061* (2013.01)

(58) Field of Classification Search
CPC ............ A61C 13/0006; A61C 13/0022; A61C 13/0004; A61C 13/0003; A61C 13/083; B23Q 3/00
See application file for complete search history.

(56) References Cited

U.S. PATENT DOCUMENTS

| | | | |
|---|---|---|---|
| 6,454,568 B1 * | 9/2002 | Beuschel | A61C 13/0003 433/163 |
| 6,739,959 B2 * | 5/2004 | Bodenmiller | A61C 13/0003 451/364 |
| 7,153,135 B1 * | 12/2006 | Thomas | A61B 5/1077 433/213 |
| 7,708,560 B2 | 5/2010 | Kraemer | |
| 8,568,897 B2 | 10/2013 | Ganley | |
| 8,751,031 B2 | 6/2014 | Sager | |
| 8,784,021 B2 * | 7/2014 | Luksch | A61C 13/0022 409/132 |

(Continued)

FOREIGN PATENT DOCUMENTS

| | | | |
|---|---|---|---|
| DE | 10233314 B4 * | 9/2007 | A61C 13/0004 |
| EP | 1088526 A3 * | 12/2003 | A61C 13/0004 |

(Continued)

*Primary Examiner* — Jacob J Cigna
(74) *Attorney, Agent, or Firm* — Dianne Burkhard

(57) ABSTRACT

A system is disclosed for processing a plurality of customized dental restorations in an automated process that comprises a milling center, a carrier for holding a plurality of customized dental restorations, and a transfer system for transferring the customized restorations between processing units. Processing units may comprise one or more of a separating unit, a scrap disposal unit, a heating unit and a cooling unit. A multi-compartment tray and a material block are disclosed for use in the system.

20 Claims, 21 Drawing Sheets

(56) References Cited

U.S. PATENT DOCUMENTS

2006/0115794 A1    6/2006  Sager
2015/0086939 A1*  3/2015  Fisker .................. A61C 9/0053
                                            433/29

FOREIGN PATENT DOCUMENTS

EP            1658825 B1    12/2016
WO    WO-2011159520 A2 *  12/2011  ......... A61C 13/0013

* cited by examiner

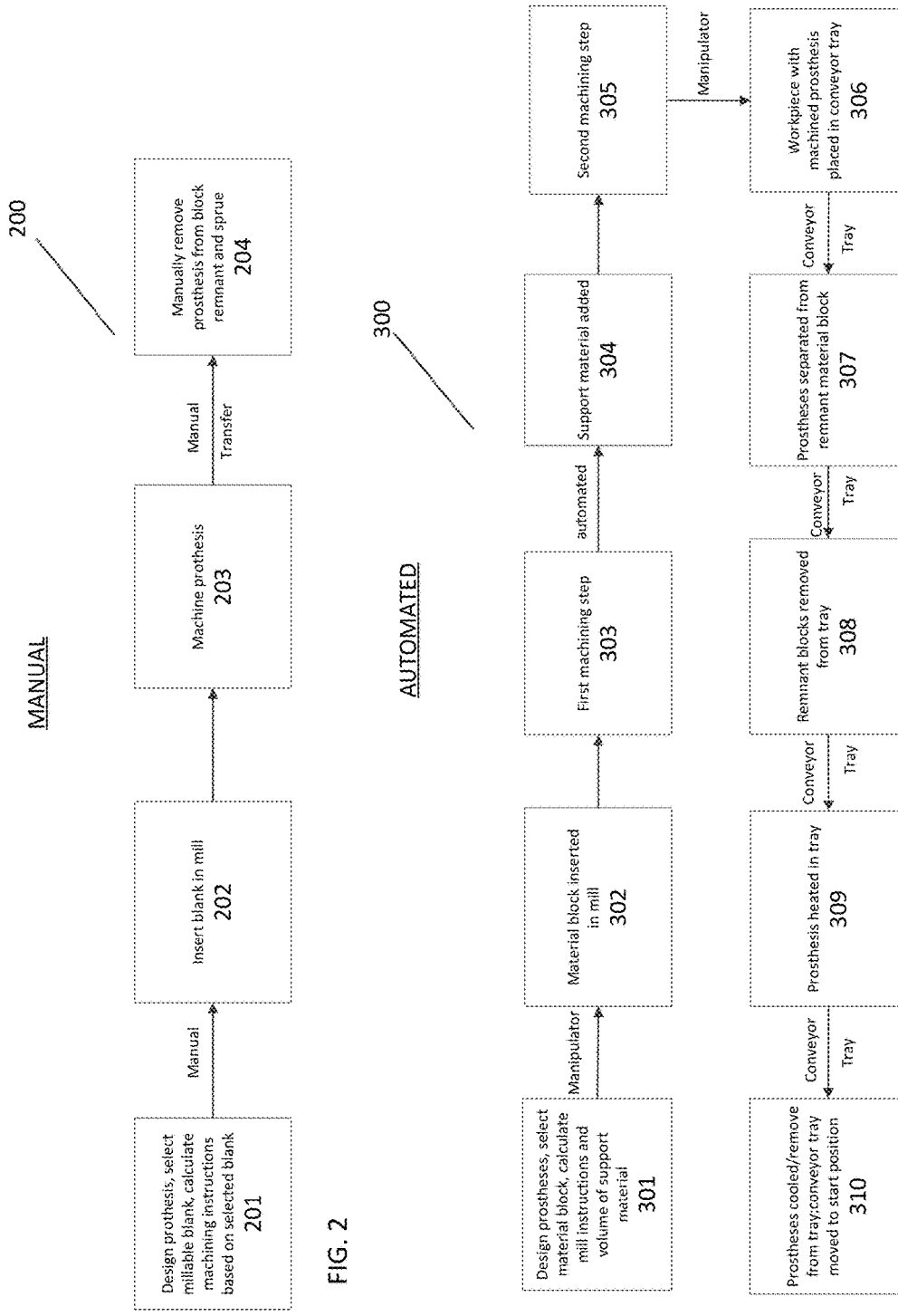

CONTINUOUS CUSTOM DENTAL RESTORATION MANUFACTURING PROCESS AND SYSTEM

This patent application claims the benefit of and priority to U.S. Provisional Patent Application No. 62/262,616, filed Dec. 3, 2015, the entirety of which application is incorporated herein by reference.

FIELD

The present disclosure relates to automation systems and automated methods for manufacturing custom dental prostheses.

BACKGROUND

Dental prostheses are typically manufactured at specialized dental laboratories that employ computer-aided design (CAD) and computer-aided manufacturing (CAM) milling systems to produce dental prostheses according to patient-specific specifications provided by dentists. In a typical work flow, information about the oral situation of a patient is received from a dentist, and the dentist or dental laboratory designs the dental prosthesis. Where the prosthesis is milled from a block of material, a material block having a size, shape, color, and material-type properties suitable for creating the prosthesis is selected. In conventional batch manufacturing processes, multiple restorations that share properties of color and material type may be milled from a single block of material, delaying production until sufficient restoration designs are ready to be milled from a single multi-unit block.

Materials suitable for use in milling into complete restorations include pre-sintered ceramic blocks, each of which have unique predetermined shrinkage information corresponding to a factor by which the material block will shrink when fully sintered. Many conventional dental milling systems determine a numerical code for machining the dental prosthesis that accounts for the unique shrinkage information associated with the assigned material block, tying production of the dental prosthesis to the assigned material block. Thus, a given dental prosthesis cannot be manufactured until the specified material block is placed in a milling machine, which can slow production of dental prostheses, and reduce system resiliency in the event of machine or material failure In conventional processes, once milled blocks are manually retrieved from the mill by a technician, material sprues that hold the restorations to the remaining material block are manually removed. Separating milled restorations from remnant block material and removing sprues from the milled restoration by manual techniques delays completion of the final restoration and introduces the potential that the final restoration will deviate from the original design. Subsequently, restorations are sintered, and then may be stained and glazed before being returned to the dentist for placement in the mouth of a patient. Accordingly, improvements to dental milling processes and systems are desirable.

SUMMARY

Certain embodiments of the disclosure concern systems and methods for manufacturing dental prostheses by automated processes are disclosed. An automated manufacturing process and a system are described wherein a plurality of custom dental restorations, made by CAD/CAM techniques, are volume-processed without hand-finishing by a technician. Novel hands-free processing units, disclosed herein minimize deviations from a CAD design that may affect the fitment of the final restoration. An automated process may include one or more hands-free, automated steps, including designing dental prostheses using CAD systems that may be local or over a network, transferring material blocks to a mill unit by way of a manipulator, adding support material to material blocks, removing workpieces from the mill and transferring workpieces to a carrier, separating a plurality of custom dental prostheses from remnant material blocks, disposing of remnant material blocks, and heating the separated prostheses, thereby increasing production and minimizing errors attributable to non-automated processing. In an embodiment, a method is provided for the volume processing of a plurality of custom prostheses, wherein multiple custom restoration designs are simultaneously manufactured into dental prostheses by automated process steps described herein.

In another representative embodiment, a system comprises a dental prosthesis database to receive and store data concerning a custom dental prosthesis, over a network. A machining instructions tool may be provided to determine machining instructions based at least in part on a nominal enlargement factor for a selected material type of a material block. The system further includes a dental prosthesis selection module to associate machining instructions with a milling unit based on a request from the milling unit for information regarding a dental prosthesis to be milled, a controller to select a material block for the custom dental prosthesis, to modify the machining instructions according to the actual enlargement factor of the block, and optionally, to determine the volume of support material to be added during the machining process, to direct a manipulator to remove a workpiece containing the custom dental restoration from a milling unit, and to place a plurality of custom workpieces from one or more milling units into identified tray compartments, and to associate a tray compartment with a custom dental prostheses during one or more automated manufacturing process steps. In one embodiment, a mill unit in communication with the controller, can receive machining instructions to machine a first side of a material block to form a portion of the dental prosthesis, to introduce support material to a milled recess in the material block, and subsequently, to mill a second surface of a material block to form the custom dental prosthesis that is supported by the support material. Machining instructions based on either the nominal or actual enlargement factors optionally, may be used to calculate a volume of support introduces during the milling process. The volume of support material may be determined from the volume of material to be removed from a first side of a material block.

Another representative embodiment includes one or more non-transitory computer-readable media storing computer executable instructions for causing a computer to perform a method, the method comprising over a network, receiving data concerning a dental prosthesis, selecting a material from which to machine the dental prosthesis, determining machining instructions for machining the dental prosthesis based on a nominal enlargement factor corresponding to the selected material, and determining instructions for adding support material during the milling process, optionally, based on data concerning the dental prosthesis and the selected material. The method may further comprise steps for storing the machining instructions, receiving a request from a mill unit for a dental prosthesis to be milled by the mill unit, associating the dental prosthesis with the mill unit, selecting a material block comprised of the selected material, and determining a material block actual enlargement factor of the selected material block. The method can further comprise modifying the machining instructions according to a difference between the nominal enlargement factor and the material block actual enlargement factor, and machining the dental prosthesis according to the modified machining instructions. The method may further comprise the steps for providing instructions for transferring workpieces to a tray and a process for tracking a plurality of custom dental prostheses through subsequent process steps.

The foregoing and other objects, features, and advantages of the disclosed embodiments will become more apparent from the following detailed description, which proceeds with reference to the accompanying figures.

BRIEF DESCRIPTION OF THE DRAWINGS

FIG. 2 is a flowchart of a known manual process for making a dental restoration.

FIG. 3 is a flowchart of a continuous process for making a dental restoration according to one embodiment described herein.

DETAILED DESCRIPTION

Figure 1A:
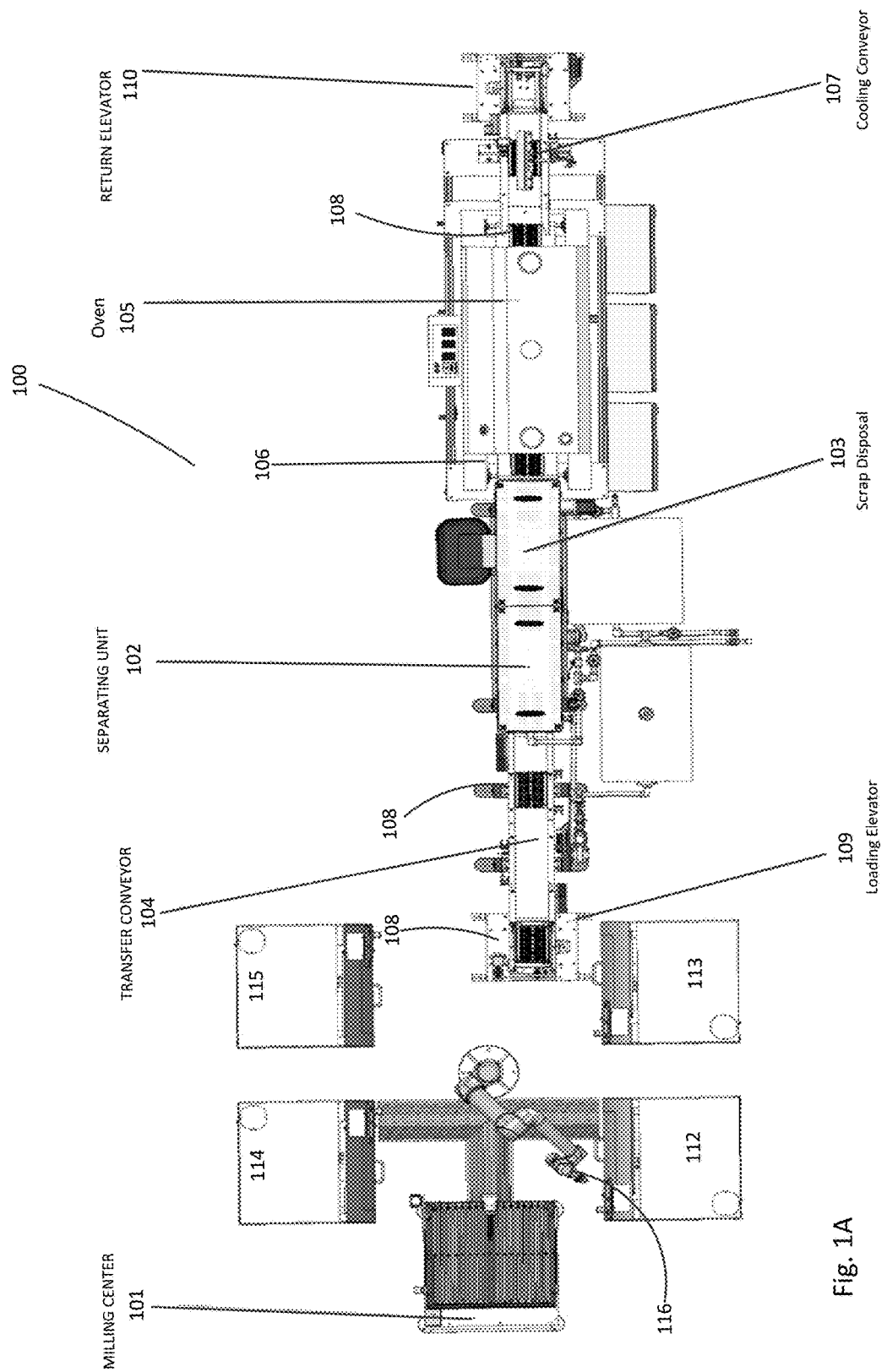
FIG. 1A is a plan view of a representative embodiment of a dental restoration manufacturing system.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

As used in this application and in the claims, the singular forms "a," "an," and "the" include the plural forms unless the context clearly dictates otherwise. Additionally, the term "includes" means "comprises."

In the following description, certain terms may be used such as "up," "down," "upper," "lower," "horizontal," "vertical," "left," "right," and the like. These terms are used, where applicable, to provide some clarity of description when dealing with relative relationships. These terms are not intended to imply absolute relationships, positions, and/or orientations, unless a particular orientation is required by specific language set forth below. For example, with respect to an object, an "upper" surface can become a "lower" surface simply by turning the object over.

A system and method for automated manufacturing of custom dental prostheses is provided. In an overview of one embodiment, exemplified in FIG. 1A and FIG. 1B, a method and system 100 are provided for the volume manufacturing of a plurality of individually designed custom dental prostheses in a continuous automated process. Information concerning proposed custom dental prostheses is received by a dental prosthesis management system that is in communication with an automated manufacturing system 100. Process stations are provided that include a milling center 101 for milling material blocks and forming custom dental prostheses according to design files. A separating station 102 is provided for separating workpieces into milled custom dental prostheses and remnant material blocks, and a scrap disposal station 103 may be provided to remove and eliminate remnant material blocks from further processing steps. A transfer system, such as a conveyor system 104 that comprises one or more conveyor units, automatically and/or simultaneously transfers a plurality of custom dental prostheses between remaining, post-milling process stations. Each process station may comprise a different transfer unit, or a different conveyor suitable to the environmental conditions of the process. Optionally, additional process stations may be included in the automated system, including an annealing station 105 for thermal treatment, and/or a cooling unit 107.

A carrier may be provided to move material blocks and dental restorations between processing units. In one embodiment, the carrier comprises a novel tray 108 having a structure that is configured to interface with each process station, including individual compartments to separate and track a plurality of custom milled workpieces for simultaneous processing into custom dental prostheses in a hands-free, automated process. Multiple tray compartments may be provided to hold a plurality of workpieces in a specified location and orientation for processing through the plurality of process stations. Each station, such as the separating unit and scrap disposal unit, may comprise devices having components in spaced arrangements that align with the tray compartments and with the orientation of workpieces held within the compartments. The assignment of an individual workpiece to a specific tray compartment isolates each workpiece and identifies the custom dental prostheses throughout the automated process until removal of the prostheses from the tray, for accurate association of each custom dental prosthesis with corresponding dental prosthesis information.

A dental prosthesis management system may receive dental prosthesis information associated with a proposed custom dental prosthesis to be processed by the dental milling center 101. The dental prosthesis management system may organize automation of prosthesis manufacturing in a first-in-first-out data structure. Requests of a plurality of dental prostheses may be processed and executed in the order in which their associated dental prosthesis information is received by the dental prosthesis management system. Alternatively, the prostheses requests may be executed by another prioritization scheme based on, for example, material availability.

The dental prosthesis management system may comprise a system capable of performing tasks related to the manufacture of dental prostheses, and can be implemented on a computer system, such as a server. The dental prosthesis management system may include a module for selecting dental prostheses, a machining instructions tool, and a dental prosthesis database. The machining instructions tool, in turn, may include more than one data base for storing information related to the modules or materials used within the system and information pertaining to the custom dental prosthesis, and machining instructions. Databases may be internal to the dental prosthesis management system, located on an external device connected to the dental prosthesis management system, or located remotely, such as in cloud-based storage.

Information used to design and/or manufacture a dental prosthesis for a patient may be received by the dental prosthesis management system from a dentist or dental office. In some representative examples, a dentist or dental office will provide information concerning the oral situation of a patient, such as a physical impression or an electronic file containing a digital scan of the patient's oral situation. Additionally, the dentist or dental office may also provide instructions for the material or materials to be used to manufacture the prosthesis, the type and construction of the prosthesis, the shade or other aesthetic features for the prosthesis, and the like. As used herein, the term "dental prosthesis" refers to any dental restorative including, without limitation, crowns, bridges, dentures, partial dentures, implants, onlays, inlays, or veneers, to name a few.

A custom dental restoration design based on the received patient information may be created with a design software package such as FastDesign™ dental design software available from IOS Technologies, Inc. of San Diego, Calif. The restoration design and other information relating to the dental prosthesis information can be passed to the machining instructions tool which can select the material type from which the dental prosthesis is to be manufactured (based on, for example, a material specified by the dentist or determined according to the type, size, etc., of the dental prosthesis). CAD/CAM machining instructions (also referred to as "numerical code" or "NC code") are determined based upon the type of restoration, the digital design of the dental prosthesis, and the selected material block.

In some embodiments, information regarding the selected material block is used for calculating machining instructions, and is stored in a database of the dental prosthesis management system. For example, material blocks that undergo dimensional reduction after milling and sintering are associated with material-specific information in order to accurately calculate machining instructions to derive the dimensions of an enlarged prosthesis milled from a pre-sintered block. The information regarding the material properties of the specific material that is used in the milling calculations may be associated with the material, and stored in a data base until the material block is selected and the information is retrieved.

By way of example, a material block may comprise a ceramic material in a pre-sintered or partially sintered state for ease in milling. After milling, the pre-sintered or partially sintered dental prosthesis is fully sintered to harden the dental prostheses. Where the final sintering process causes a dimensional reduction in the pre-sintered or partially sintered dental prostheses, the pre-sintered prosthesis is milled at a size larger than the desired size of the final restoration. An approximate enlargement factor may be derived theoretically from known properties of the material used in the block. A nominal enlargement factor for a given material type may be derived empirically as the average value of enlargement factors corresponding to respective material samples. For example, the enlargement factor of a ceramic material block may range in value from about 1.1 to about 1.3. A zirconia-based ceramic may have an enlargement factor typically ranging from about 1.21 to about 1.24, and may be assigned the nominal enlargement factor of about 1.225.

A plurality of nominal enlargement factors corresponding to a plurality of materials may be stored in a database, for later retrieval. A machining instructions tool can then determine machining instructions (for example, numerical code) for machining the dental prosthesis according to the nominal enlargement factor, and store the machining instructions in the machining instructions database. These initial machining instructions generated based on the nominal enlargement factor may be later adjusted (via a correction factor) to account for the difference between the nominal enlargement factor and the actual enlargement factor for the specific material block being used to generate the dental prosthesis.

A specific enlargement factor may be derived for each material block via measurements (e.g., physical dimensions, displacement, and weight) of a specific material block. In some exemplary embodiments, an enlargement factor is determined based upon volumetric measurements. Where the target densities of many sintered ceramic materials (e.g., zirconia) are known, the amount of shrinkage that occurs during sintering may be predicted very accurately. For example, the size of a milling block may be measured using a coordinate measuring machine (CMM) or other device to obtain a volume of the block, and its weight may be measured. From these measurements, the density of the pre-sintered or partially sintered milling block may be ascertained. The enlargement factor for the milling block is then calculated as the cube root of the ratio of the target density to the (measured) pre-sintered or partially sintered density:

$$EF = \sqrt[3]{\frac{\rho(\text{fully densified})}{\rho(\text{pre-sintered})}}$$

The final machining instructions for machining the dental prosthesis may therefore account for a nominal enlargement factor corresponding to the material block type, and/or a unique enlargement factor of the specific material block from which the dental prosthesis will be milled. In one exemplary embodiment, a representative dental prosthesis may be milled from a zirconia-based ceramic in which a nominal enlargement factor of, for example, 1.225, is used to calculate machining instructions. If the selected material block has an associated material block enlargement factor of, for example, 1.230, then a correction factor of about 1.005 can be used to modify the machining instructions and store the modified machining instructions.

Advantageously, by storing machining instructions according to a nominal enlargement factor and subsequently modifying the machining instructions according to a specific enlargement factor associated with a particular material block, flexibility and resiliency is provided to the system. Because milling instructions for a dental prosthesis milling jobs are not tied to a specific material block, the prospective dental prosthesis can be distributed to any available milling machine in the system at any time. Because a milling job can be easily routed to a second mill or milling center, as needed, and the machining instructions for that dental prosthesis can be modified according to an enlargement factor of another material block available for use by that second mill or mill group, minimal human intervention is required.

A conventional workflow 200 for producing dental prostheses, is shown in FIG. 2. A dental prosthesis is designed, and milling instructions are calculated for prostheses based on specific information for a selected material block 201. The selected mill block is inserted and removed from a milling machine manually (202 and 204). Milling instructions for the dental prosthesis are tied to the specific mill block, and are therefore arranged in a specific order for processing by a mill 203. Any change in the selected material block requires recalculation based on shrinkage of a new block.

FIG. 3 provides an embodiment of a workflow for an automated system 300 as described herein. A dental prosthesis is designed from patient specific data, and milling instructions are determined based on the material block selection 301. Dental prostheses milling jobs may be processed as mills become available, at which time a specific material block is obtained for insertion into an identified mill by a manipulator 302. In one embodiment, where the selected material block undergoes dimensional reduction post-sintering, milling instructions calculated from a nominal enlargement factor based on the selected material type, may be modified according to the specific enlargement factor associated with the selected material block. Milling instructions may be used to calculate a volume of a support material to be dispensed during the milling process. Instructions for milling a material block may be divided into two or more milling steps, 303 and 305, and a further step for adding a volume of support material 304 between milling steps 303 and 305.

Figure 4:
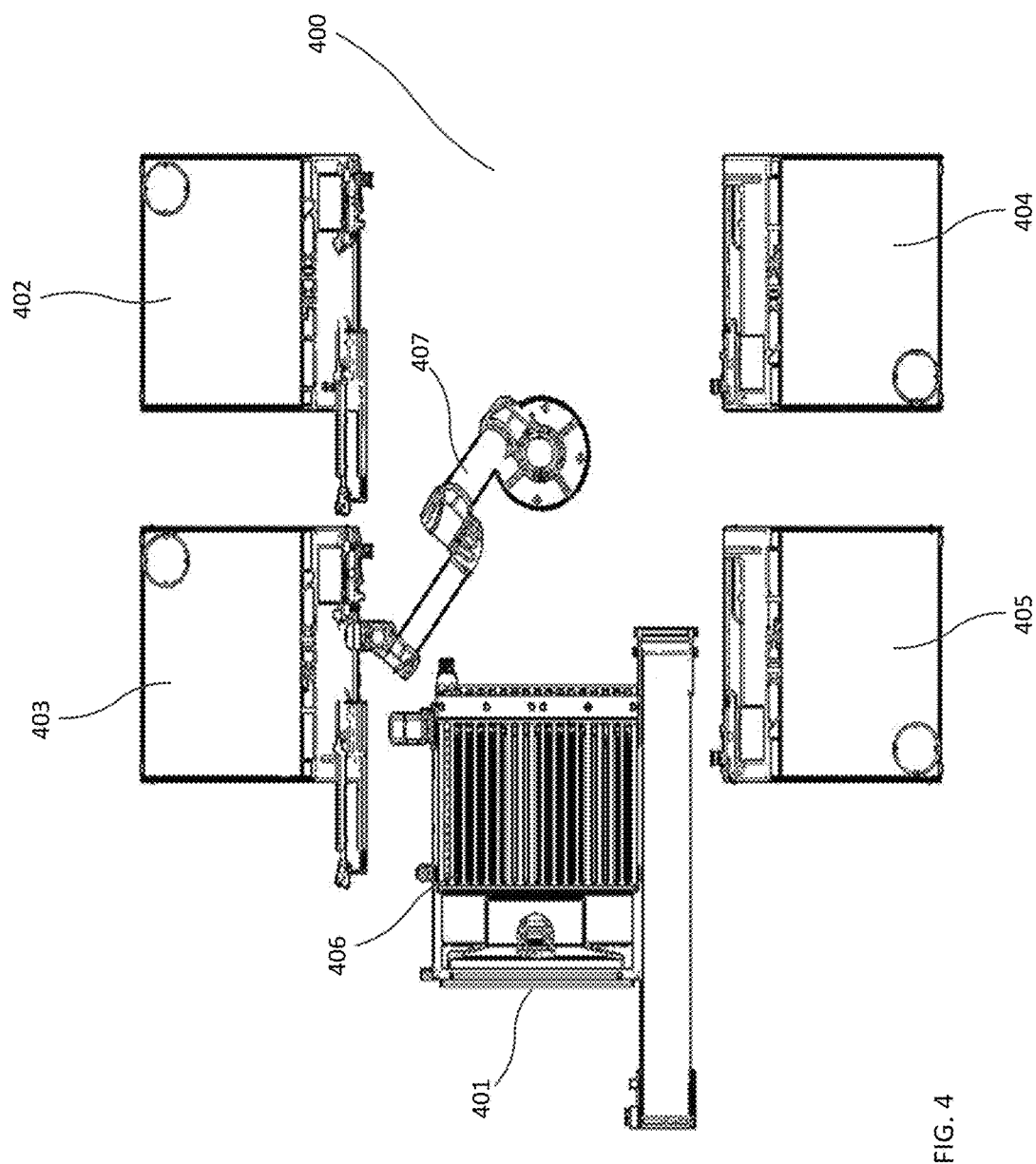
FIG. 4 is a plan view of a representative embodiment of a dental milling system of a continuous dental restoration system.

FIG. 4 illustrates an exemplary embodiment of a milling center 400 that may be used in the automated system for making dental prostheses. The operation of the milling center may be controlled by a dental prosthesis management system that is in communication with the milling center. The dental prosthesis management system may comprise a selection module for selecting a specific material block, and a machining instructions tool to coordinate the operation of the milling center to produce dental prostheses. A monitor 401 may optionally display information from the dental prosthesis management system including material inventory information, queue information, status of individual mills and prosthesis production, optionally allowing for input by a user.

The milling center 400 may comprise a plurality of milling machines, for example 402, 403, 404 and 405 (also referred to as "mills"), a material block rack 406, a manipulator 407, and a mill group control module that coordinates the operation of the milling machines (e.g., 402-405) with the rack 406 and the manipulator 407. FIG. 4 illustrates an exemplary milling center that includes four milling machines, however milling centers comprised of one, two, three, five, six, seven or eight, or more than eight, milling machines may be suitable for use in the system and process described herein. A plurality of material blocks may be inventoried in the material block rack 406. A representative method for milling is described in commonly owned U.S. patent application Ser. No. 14/674,629, (filed Mar. 31, 2015), which is hereby incorporated by reference in its entirety.

Suitable millable material blocks may comprise material bodies that have a cube, prism, cylindrical or disc shape, having curved or flat surfaces, such as blocks having surface shapes that include square, oblong, rectangular, curved, circular, or triangular-shaped surfaces. Other geometric or non-geometric shapes or forms from which a dental prosthesis may be shaped may also be suitable for use herein. The material block may comprise a holder attached to one side, or more than one side, of the block, for example, by adhesive or mechanical means. In one embodiment, a mandrel attaches to a side or surface of a mill block, for example, by adhesive, for placement in a mill.

Figure 5A:
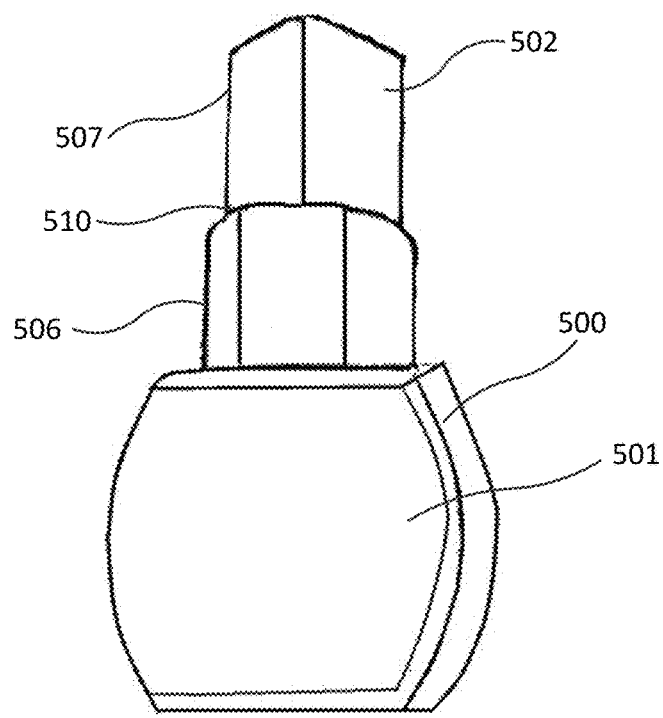
FIG. 5A is a representative embodiment of a material block suitable for use in one embodiment of a process described herein.

Exemplified in FIG. 5A, a material block 500 for milling a single restoration such as crowns, is depicted. The block material body, as illustrated, comprises a flat upper milling surface 501 and a flat lower milling surface 503, that are accessible by a milling tool for commencing milling instructions. Upper and lower surfaces are depicted as flat surfaces joined by two opposing curved side surfaces, and having a top end and an opposing bottom end that is attached to a mandrel 502 to secure in a mill during a machining process. Another material block suitable for use in forming multi-unit restorations is exemplified in FIG. 5C, which is depicted as having flat upper and lower millable surfaces joined by straight side surfaces, and a top end and an opposing bottom end to which a mandrel 502 is attached. The material block 500 may include a barcode, for example, on the body of material or on the mandrel 502, to provide specific information regarding the material block, such as the material type, color or shade, and/or actual enlargement factor specific to the individual material block.

A mandrel may comprise two elongated portions along a common axis (A-A) for securing in the mill unit and transferring into and out of the tray. Optionally, the mandrel fits through an opening in a tray wall separating the first and second compartment areas. The mandrel comprises a first elongated portion 506 having a first end 508 that is attached to the bottom surface of the material block portion and an opposing second end 510 optionally comprising a shoulder. The second elongated portion 507 is adjacent the first elongated portion 506 at a second end 510 of the first elongated portion. The second elongated portion 507 optionally, has a cross-sectional geometry that is smaller than the first elongated portion 506 for the length of the second portion. Optionally, the first elongated portion 506 ends at the shoulder which extends beyond the exterior geometry of the second elongated portion. The first elongated portion optionally, comprises at least one planar surface 511, or optionally, two opposing planar surfaces. The second elongated portion has at least one planar surface that is not orthogonal to a planar surface of the first elongated portion. Optionally, the second elongated portion as two adjacent planar surfaces, and optionally, the two adjacent planar surfaces are not orthogonal the flat surfaces of the first elongated portion.

A material block for making a prosthesis may be comprised of any material, or combinations of materials, suitable for machining into a dental restoration. In some embodiments, the material block comprises biocompatible ceramic, including silica-, alumina-, leucite-, and/or zirconia-based ceramics, or any combination thereof. Blocks may comprise other machinable materials such as glass, or glass ceramics, polymeric composite materials, chrome cobalt. In one representative embodiment, material blocks comprise BruxZir® zirconia millable blocks available from Glidewell Laboratories (Irvine, Calif.).

Figure 1B:
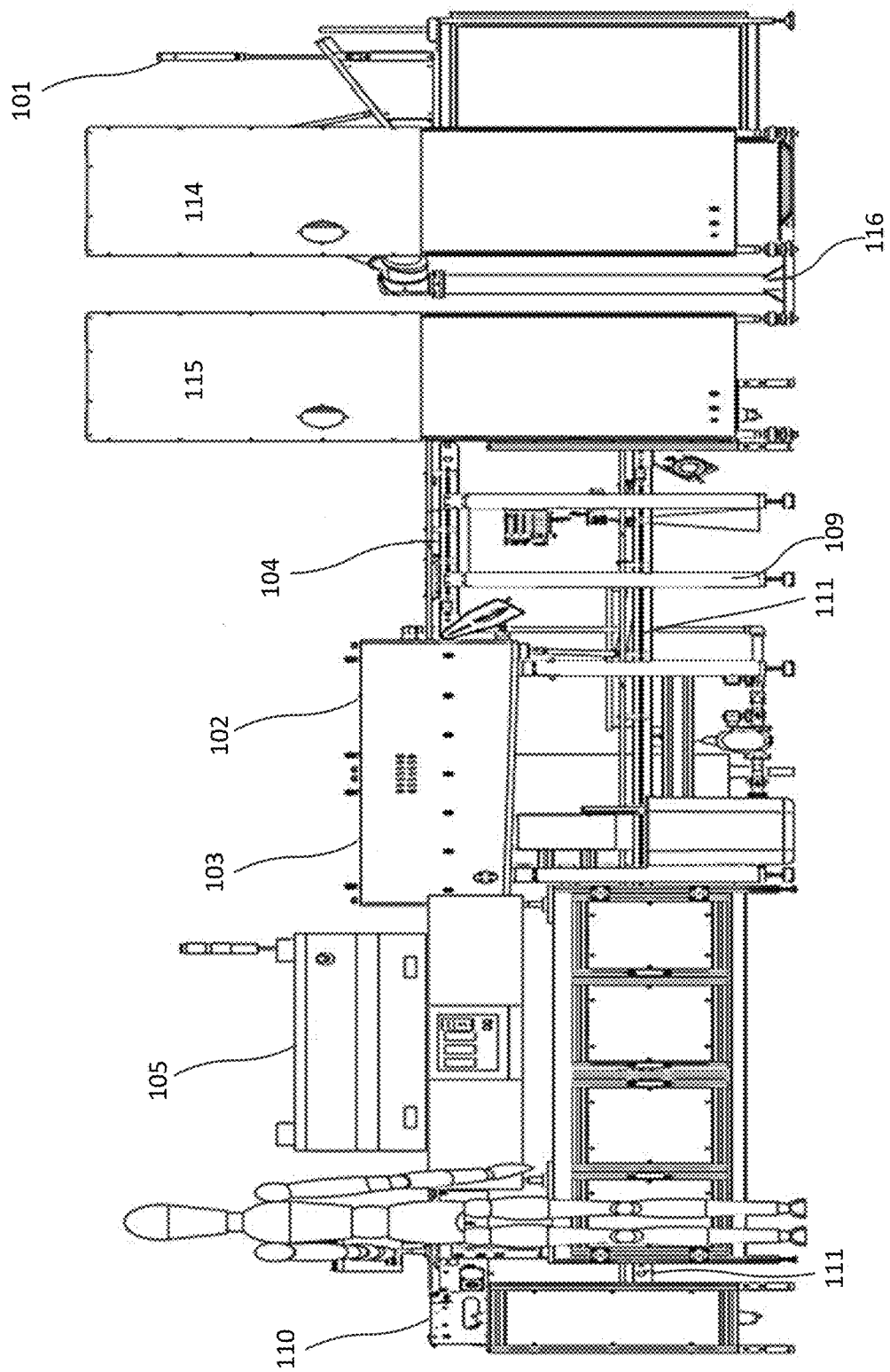
FIG. 1B is a front view of a representative embodiment of a dental restoration manufacturing system.

A mill group control module can receive the machining instructions associated with a specific dental prosthesis, and information such as a nominal enlargement factor of a specified material type, which can be stored in the machining instructions database. The dental prosthesis management system may provide instructions to the control module to cause an automatic device, or manipulator 407, to pick a material block from the rack 406, and obtain material block information (for example, by scanning a barcode associated with the material block), and place the material block in the available mill (e.g., 402, 403, 404, or 405). In some embodiments, the manipulator 407, may be an automatic parts placer, and may be robotic, pneumatic or mechanical. In some embodiments, the manipulator can be a robotic arm 116, as shown in FIG. 1A. In some embodiments, the manipulator 407 and/or milling machines (e.g., 402-405) into which the material block is placed, has a barcode reader or other device to scan the barcode associated with the material block, and transmit information concerning the material block to the dental prosthesis management system. Material block information, such as an actual enlargement factor, can be returned to the control module and stored as one or more entries in the material block information database. The machining instructions modification tool can then determine a correction factor that represents a difference between the nominal enlargement factor used to determine the machining instructions and the material block actual enlargement factor.

In a conventional process 200, restoration designs are executed in CAM systems upon selection of material blocks manually inserted in to a mill 202. In conventional processes, prostheses are milled according to machine instructions 203 which provide for the inclusion of sprues and/or connectors. Sprues or connectors that connect the prosthesis to the block are milled forming a bridge of continuous block material preventing the prosthesis from falling from the workpiece. Because sprue placement is often customized to an individual restoration tooth, the process of removing the sprue is unique to each restoration, requiring manual intervention to separate a restoration from a remnant mill block. Thus, after milling, prostheses are separated from the connectors or sprues by technicians using hand tools, which may decrease the accuracy and integrity of the reproduction of the prosthetic design 204. Surfaces irregularities or protuberances from the release process are removed from the prosthesis by grinded with handheld.

In contrast to the method of FIG. 2, a method 300 is disclosed at FIG. 3, which comprises generating milling instructions 301 from a CAD file to machine a material block into a custom dental prosthesis without milling any supporting connectors or sprues (302, 303, 305). Where the resulting prosthesis material is has no supporting attachment to the remaining material block, the manual step of removing sprues or connectors by a technician is eliminated. In one embodiment, a first set of machining instruction is provided to mill a first portion of the custom dental prosthesis from the material block in a first milling step 303, without milling a sprue or connector. A second set of machining instructions is provided for introducing a volume of support material within a recess of the material block formed by the removal of block material in the first milling step. A third set of machining instructions is provide to perform a second or subsequent, milling step 305, to mill a second portion of the custom dental prosthesis, separating the material of the dental prosthesis and the block material. The support material, at least partially filling the material void between the dental prosthesis material and the remnant material block, holds the custom prosthesis in place within the recess of the material block. In a volume manufacturing process, a plurality of custom workpieces may be concurrently manufactured in the milling center, transferred to a tray and conveyed 306 through a series of process stations, where the prostheses are separated from the remnant material blocks 307. In an optional process step, the remnant block is removed from the tray 308, and the tray containing the prostheses is conveyed to a heating unit and heated to remove any residual support material 309. The tray and/or prostheses are cooled 310, and the tray is optionally conveyed to the start position.

Figure 5B:
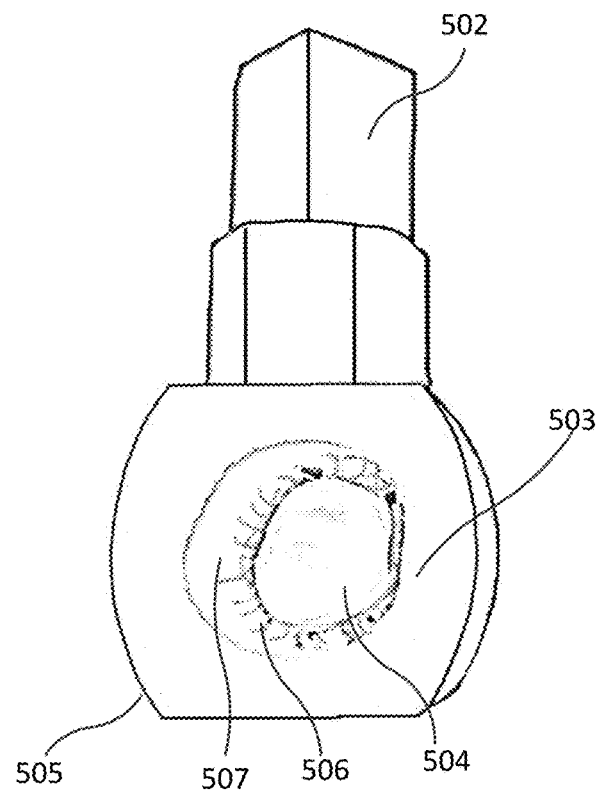
FIG. 5B is a representative embodiment of a workpiece comprising a custom dental restoration supported within a material block manufactured according to one embodiment of a process described herein.
Figure 5C:
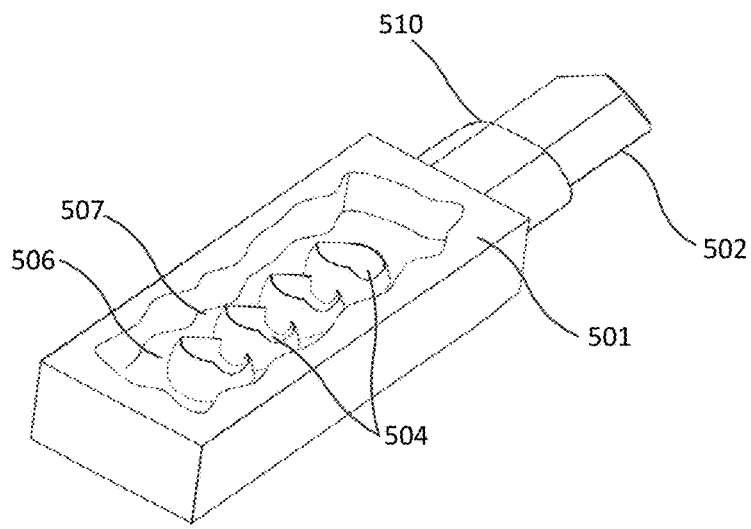
FIG. 5C is a representative embodiment of a workpiece comprising a multi-unit bridge custom dental restoration supported within a material block manufactured according to one embodiment of a process described herein.
Figure 5D:
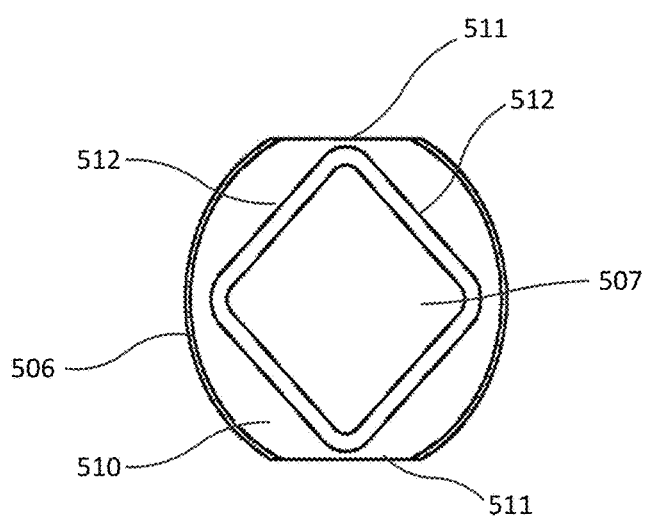
FIG. 5D is an illustration of an end view of a mandrel according to one embodiment described herein.
Figure 5E:
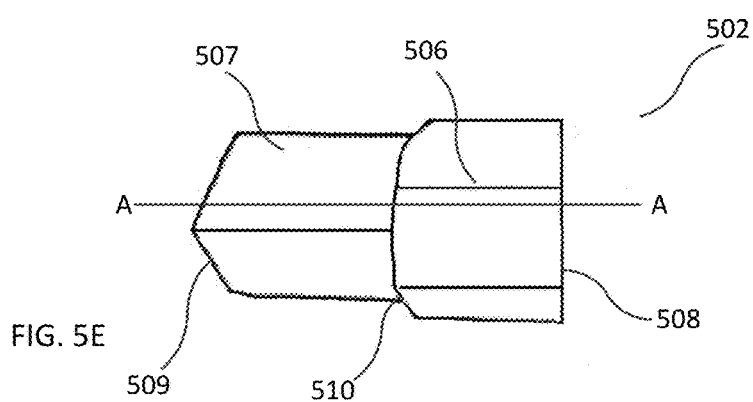
FIG. 5E is an illustration of a side view of a mandrel according to one embodiment described herein.

In FIG. 5B, an exemplary workpiece is shown that comprises the remnant of the original material block of FIG. 5A, having a recess 506, a milled dental prosthesis 504, and a support material 507 that fills at least a portion of the recess 506. The support material has sufficient strength to support the custom dental prosthesis within the recess 506, such as a crown (FIG. 5B) or a bridge (FIG. 5C) during completion of the machining cycle. A first side (e.g., upper or lower surface) of a material block 500 machined using at least one tool selected from a grinding, finishing or anatomy tool, forms a portion of the prosthesis 504. The first portion of the prosthesis may include the widest area around prosthesis perimeter, or the parting line. Support material 507 is automatically introduced into the recess 506 of the material block prior to a second machining step. A second side 503 of a material block is machined using at least one tool selected from a grinding, finishing or anatomy tool. The completed custom prosthesis is unattached to the material block except for connection via the support material.

The support material, introduced into the recess after the first milling step, may surround a portion of the perimeter of the custom restoration, for example, around the parting line. In one embodiment, the workpiece 505 is rotated between a first side (e.g. upper surface) and a second side (e.g., lower surface) between first and second machining steps to optimize accessibility by a machining tool. The support material is added and at least partially hardened between steps, and prevents the prosthesis from falling from the workpiece 505 after the prosthesis is disconnected from the material blank. As described for use herein, the internal surface of a restoration (e.g., crown) comprises the surface that is opposite the occlusal surface, and that connects to a tooth preparation of a patient; the external surface of the restoration crown is generally opposite the internal surface, and may include occlusal, and buccal/labial, lingual, mesial and/or distal side surfaces. The surfaces of the restoration may be milled in any order. In one embodiment, in a first milling step, a portion of the external surface of a restoration comprising the occlusal surface and the external side surfaces to the parting line is milled. The support material is introduced onto the occlusal surface, surround a portion of the restoration side surfaces around the perimeter. In a second milling step, the internal surface is milled, and upon milling the remainder of the external surface, the prosthesis is separated from the material block.

The dimensions of a multi-unit bridge within a material block should provide space between the bridge and the outer wall of the material block for the addition of an adequately supporting volume of support material, and to provide a minimum wall thickness to prevent warpage during milling. In one exemplary embodiment, a material block is provided having dimensions of, for example, approximately 55 mm×19 mm×23 mm. A multi-unit bridge having as its largest dimension a length less than or equal to about 45 mm provides adequate space within the recess of the milled material block for the addition of support material, and sufficient wall thickness to prevent warpage during milling.

The volume of support material introduced within a milled block recess may be standardized, and automatically dispensing as a predetermined amount for all dental restorations. Alternatively, the amount of support material may be standardized for groups of similarly sized prostheses. In a further alternate embodiment, the volume of support material added to the milled recess may be individually determined for each custom restoration based on the geometry of the patient-specific dental restoration. The volume of support material may also be determined based on the volume of block material removed from a first side. In one embodiment, patient-specific machining instructions for milling the material block are provided by the dental prosthesis management system for use in determining an amount of support material to add between machining steps. The volume of material block to be removed during a first machining step, or from a first side of a block, may be assessed to determine the volume of support material to add. The volume of support material may be based on milling instructions calculated with a nominal enlargement factor for the material block type, or with an actual enlargement factor of the material block. The ratio of the volume of support material to the volume of material block removed during the first machining step may be approximately 1:1, or the ratio may be greater than 1:1, or the ratio may be less than 1:1, depending on the nature and strength of the support material. A range of approximately 700 ml to approximately 1400 ml of support material may be suitable for use single unit restorations, such as a crown. A range of approximately 3000 ml to approximately 4500 ml of support material may be suitable for use in multi-unit restorations, such as a multi-unit bridge having, for example from about 2 to about 5 replacement restoration teeth.

The support material may be any formable material dispersed as a solid, liquid or semisolid. Exemplary embodiments of support materials comprise support materials that may be dissolved or liquefied, such as thermoplastic materials. The support material may be dispensed by a dispenser integrated near the spindle of machine mill. A dispenser integrated near the spindle may be controlled to automatically provide support material by injecting or casting a liquid after the milling of a first side of a material block is completed.

In one embodiment, a hot melt system (such as Astro Hot Melt System SS10 from Astro Packaging, Anaheim Calif.) may be used for dispensing thermoplastic support materials to one or more mills. The hot melt system may be used to control heat scheduling, and to supply heat and power to a hose and dispenser for dispensing the support material. A support material, such as a paraffin wax, may be melted by the hot melt system at a temperature of about 100° C. to about 110° C. In one embodiment, the hot melt system is gravity fed, held above the height of an automated dispensing tool, such as an automatic pneumatic gun incorporated as a component of the milling center, or individual mill. A pneumatic dispenser controlled by the mill delivers an approximate or specific amount of support material to the milled area of a material block. The mill controls the amount of support material dispensed through a heated nozzle by controlling the amount of time the dispenser is opened. For each mill the average volume of support material that is dispensed through the pneumatic dispenser for a given unit of time may be calculated. For each workpiece, the step of dispensing the support material may comprise the step of determining at the mill the volume of support material that a system will dispense in a given amount of time, determining the volume of the recess formed by removing millable block material during a first mill step from milling instructions, and calculating the amount of time to dispense support material into the recess at the given mill to dispense the selected volume of support material. Alternatively, a commercially available dispensing unit utilizing pressured air to inject liquid support material may be suitable for use herein. The dispensing unit may also comprise a heater to maintain the support material in liquid form in an airtight reservoir to maintain pressure.

Support material may harden, for example, at ambient temperatures, prior to rotating or moving the material block into position to machine remaining portions of the restoration design from a second block surface. Optionally, a blower may be incorporated at the mill to facilitate rapid hardening of the support material with air. In one embodiment, a commercially available dispenser may be provided to dispense cold or sub-zero air to liquid support material to reduce the time to solidify the support material, reducing the overall time of the machining process (available through NETFLOW; FRIGID-X trademark. Optionally, tools may be provided to the milling system for cleaning a surface of the prosthesis prior to introducing the support material. Suitable cleaning tools include a device for delivering pressurized air to blow dust from a milled surface, or a bush for brushing a milled surface.

After all machining steps are complete, the workpiece may be removed from the mill manually, or by the manipulator 116. In one embodiment, the manipulator 116 loads a plurality of custom workpieces from a single mill or a plurality of mills (for example, 112-115) onto a carrier 108 at a loading area of the transfer system. A transfer system such as a conveyor system 600 is provided for moving carriers containing workpieces between and through process stations to separate prostheses from the remnant material block. A transfer conveyor 104, 601 conveys carriers 108 containing the plurality of individually customized workpieces away from the milling center 101 and loading area onto the separating unit conveyor 902, for processing in the separating unit 102, 900. Optional guide rails 602 on either side of a conveyor and spaced according to tray dimensions, feed trays through the conveyor system 600, and between discrete conveyor belts of adjacent stations.

Figure 6:
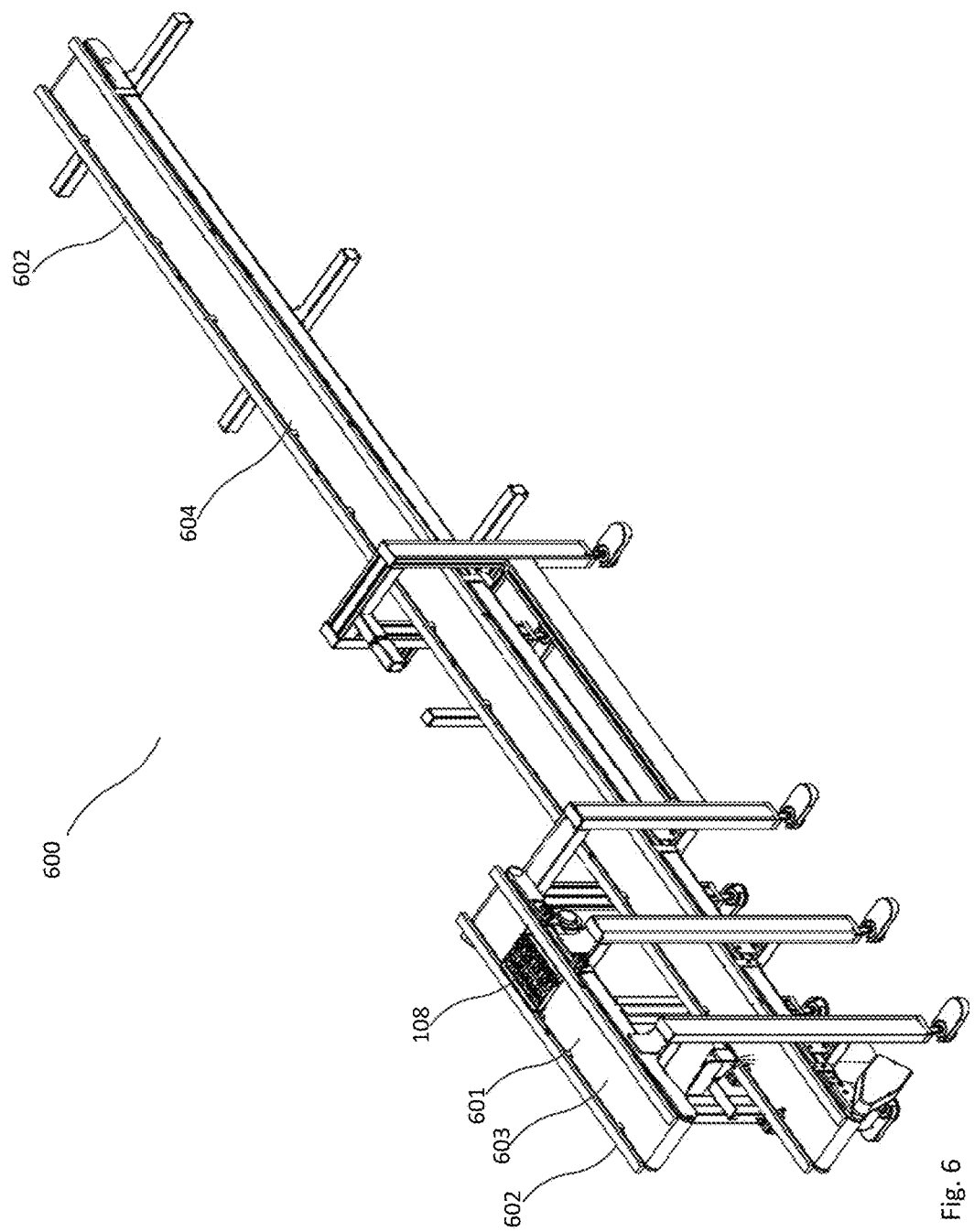
FIG. 6 is a schematic illustration of a representative embodiment of a conveyor unit of the system described herein.
Figure 8B:
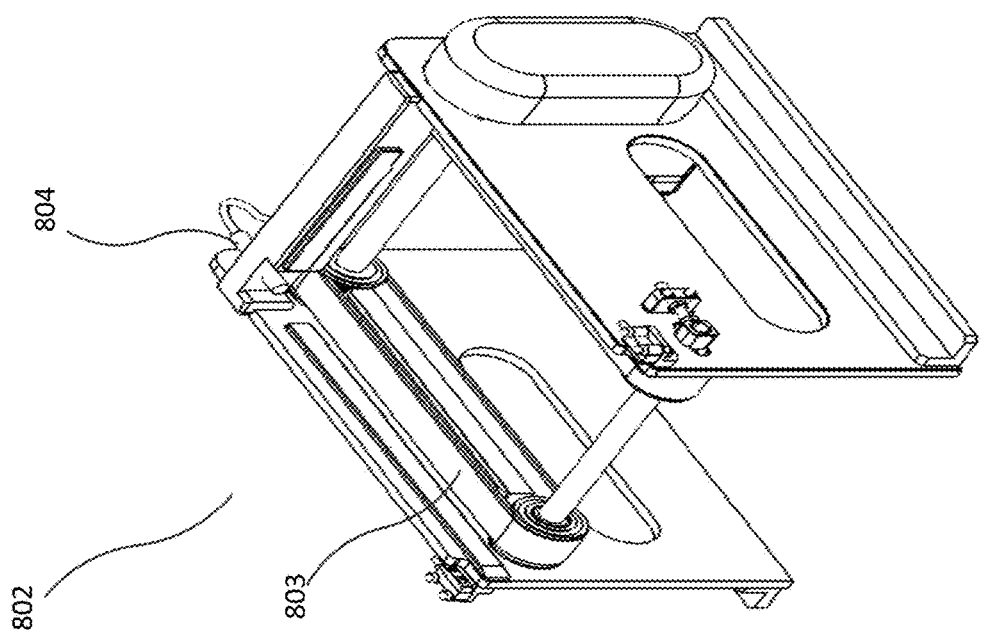
FIG. 8B is an illustration of one embodiment of a component of an elevator unit of the continuous system describe herein.
Figure 8A:
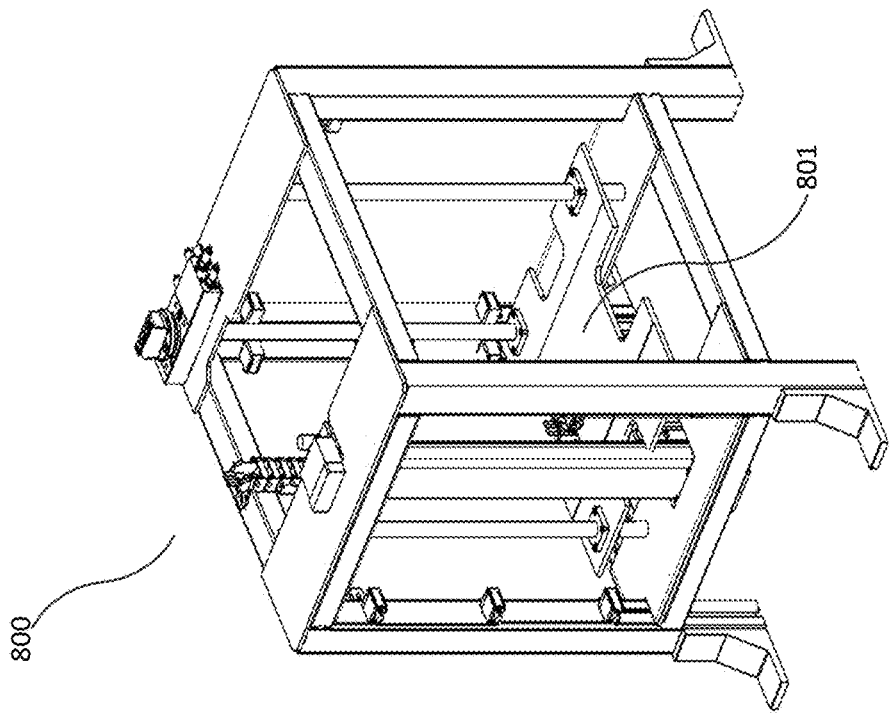
FIG. 8A is an illustration of one embodiment of a component of an elevator unit of the continuous system described herein.
Figure 9A:
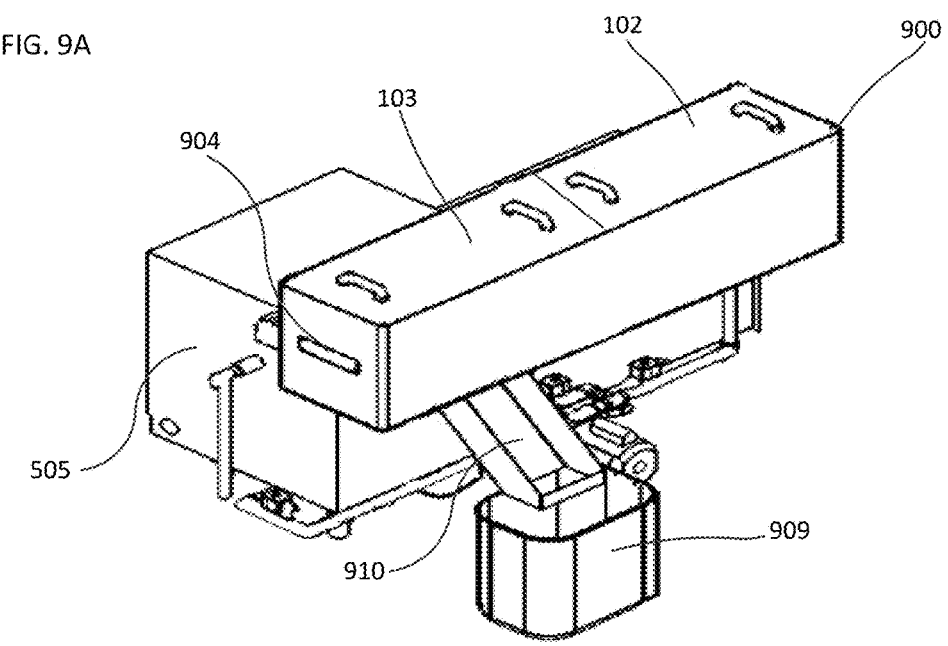
FIG. 9A is a perspective view of one embodiment of a separating unit and scrap disposal unit within a separating tank from a first side.
Figure 9B:
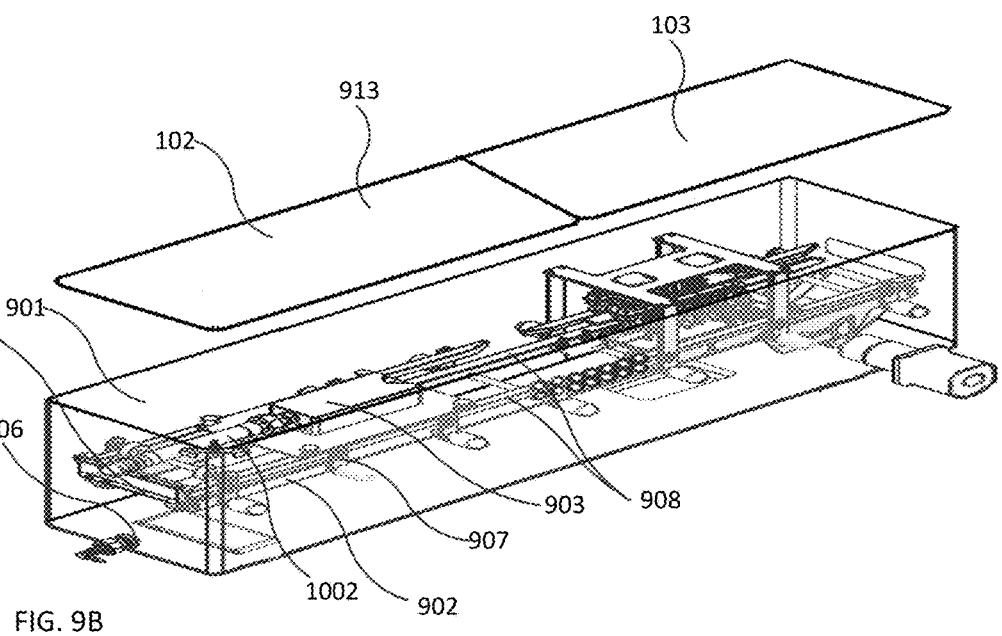
FIG. 9B is a perspective view of one embodiment of a separating unit and a scrap disposal unit within a separating tank of the continuous system described herein from a second side.
Figure 9C:
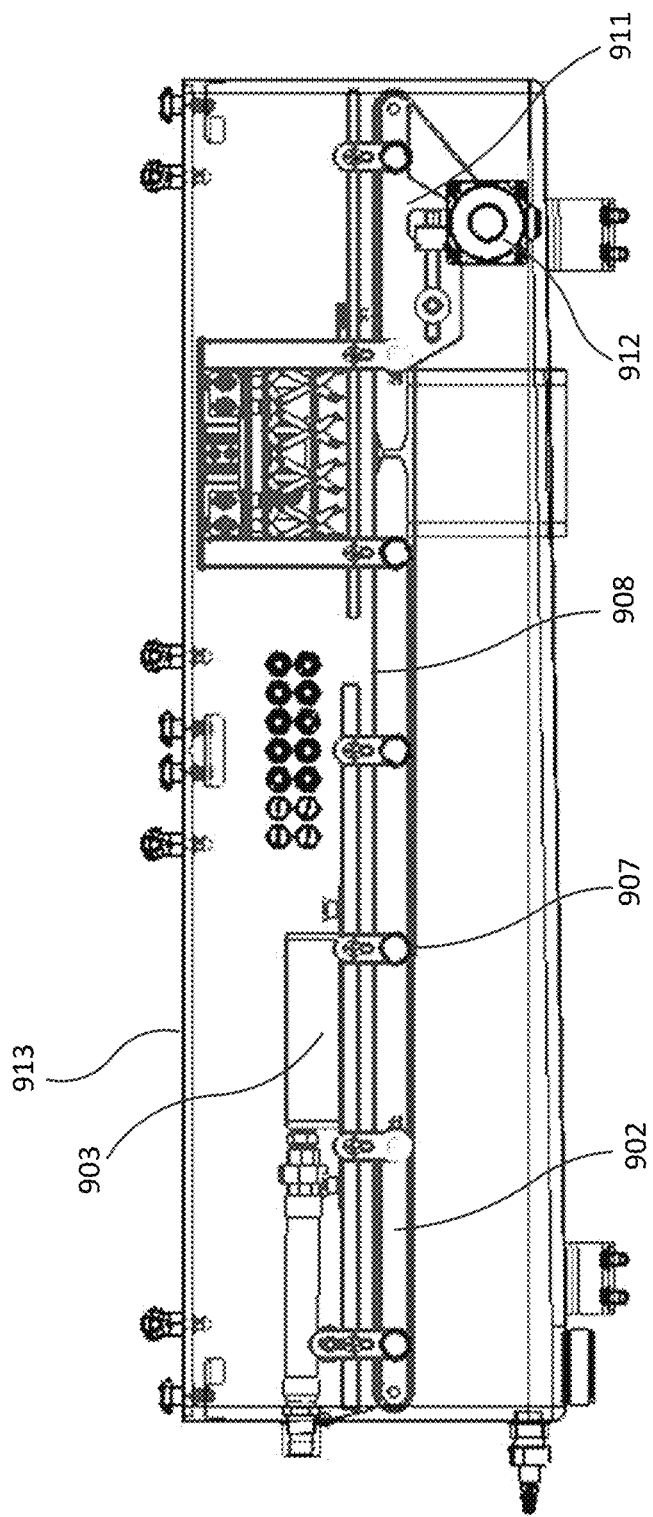
FIG. 9C is a side view of an embodiment of a separating unit and a scrap disposal unit within a separating tank of the continuous system described herein.

In one example, a return conveyor is provided that returns trays to a start position after completion of the separation process. The return conveyor may be below the transfer conveyor and processing units, as exemplified in FIG. 1B and FIG. 6. An elevator 800 comprising components illustrated in FIGS. 8A and 8B may be provided at each end of the conveyor system to lower or lift trays between conveyor belts. A loading elevator 109 provides trays in a 'start' position for loading workpieces into the tray by the manipulator. Trays 108 are conveyed via a transfer conveyor belt 603 to begin the separation process at a separating station 102. Upon completion of the separation process, emptied trays are lowered by a return elevator 110 to a return conveyor 111, 604.

The elevator 800 comprises a plate 801 that lifts or lowers a tray holder 802 between upper and lower conveyor belts of a conveyor system 600. The tray holder 802 may comprise parallel elevator belts 803 spaced according to the dimensions of the tray which is located on the belts for loading and conveying trays onto the transfer conveyor 104. One or more sensors 804 may be provided to detect a tray on the elevator tray holder 802, for example, to initiate lift/lower movement or conveyor movement of elevator components (i.e., elevator belts 803).

Figure 7A:
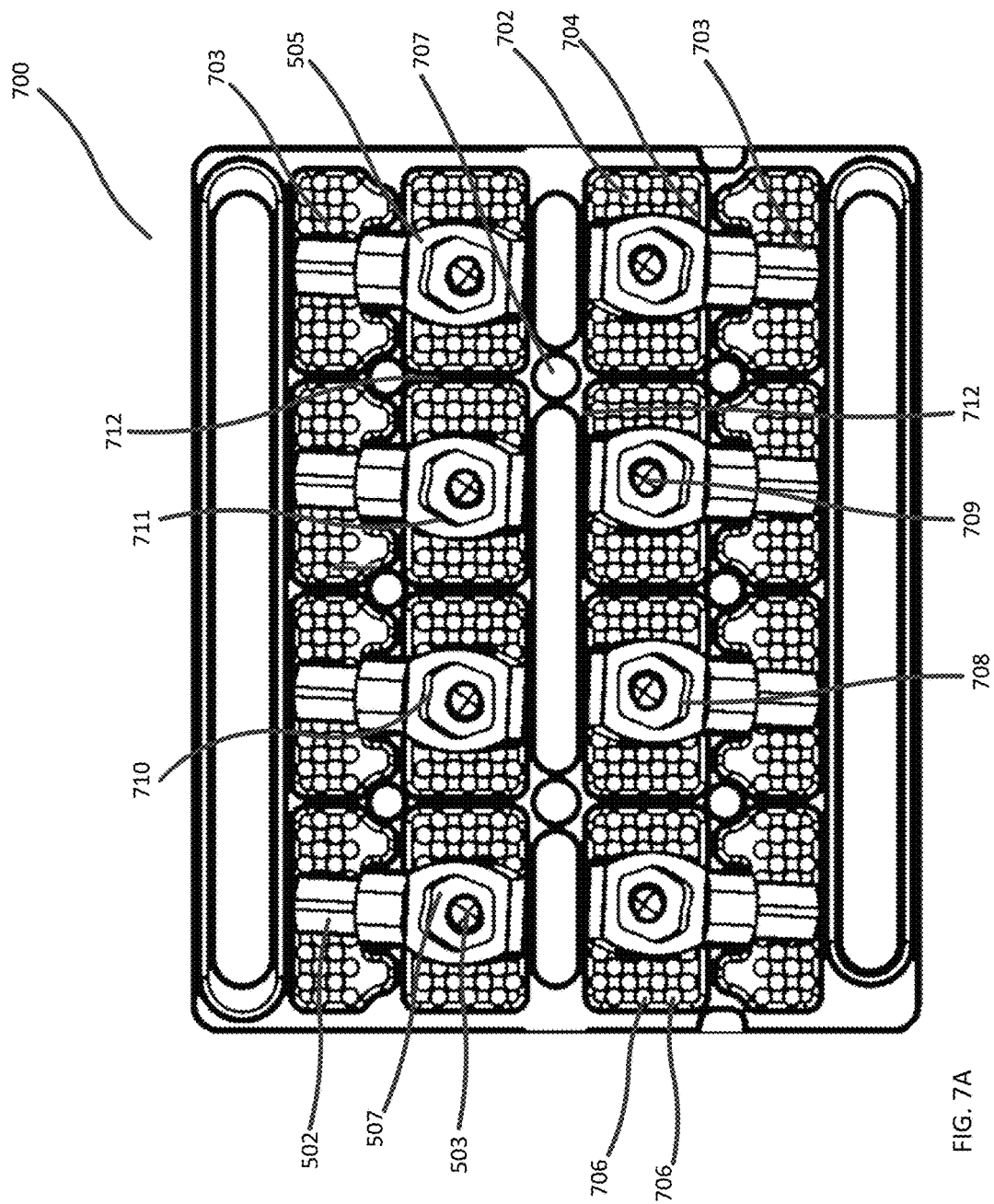
FIG. 7A is a plan view illustration of one embodiment of a tray for use in a continuous system described herein, containing workpieces.
Figure 7B:
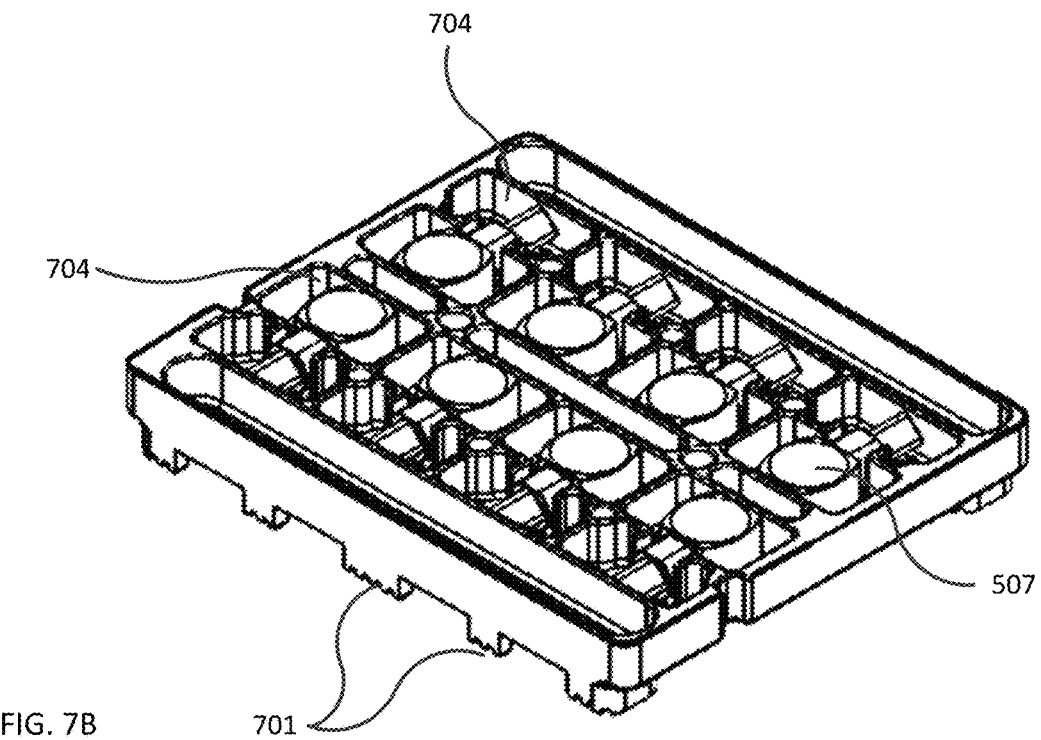
FIG. 7B is a perspective view of an illustration of one embodiment of a tray containing workpieces for use in a continuous system described herein.
Figure 7C:
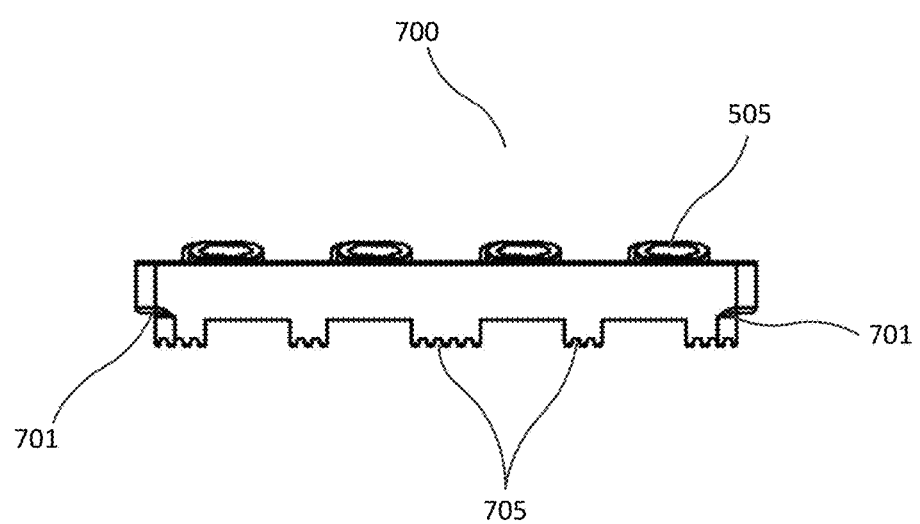
FIG. 7C is a side view illustration of one embodiment of a tray containing workpieces for use in a continuous system described herein.

FIGS. 7A-7C provide a schematic representation of multiple views of an exemplary tray 700 for conveying a plurality of workpieces 505 through the automated system. Information regarding the placement of each workpiece at an identified compartment location of a specific tray may be stored as dental prosthetic information to enable accurate identification and tracking of each custom dental device throughout the system. In one embodiment, a tray comprises a plurality of individual compartments, each compartment for holding a single workpiece, to facilitate simultaneous processing of two or more workpieces. Though the number of compartments in each tray is not critical, it may be influenced, for example, by the number of mills in the mill center, or the capacities of the separating unit, disposal unit, or oven, or the preference of the lab to complete a restoration within a particular time frame.

In some embodiments, a multi-compartment tray may comprise two, three, four, five, six, seven, or eight, individual, adjacent compartments to simultaneously process two or more workpieces. Each compartment may comprise a first compartment area 702 for holding the milled material block and a second compartment area 703 for holding a mandrel 502. A wall 704 partially separating first and second compartment areas (702,703) has an opening through which a portion of the workpiece (for example, the mandrel 502) passes.

Figure 7D:
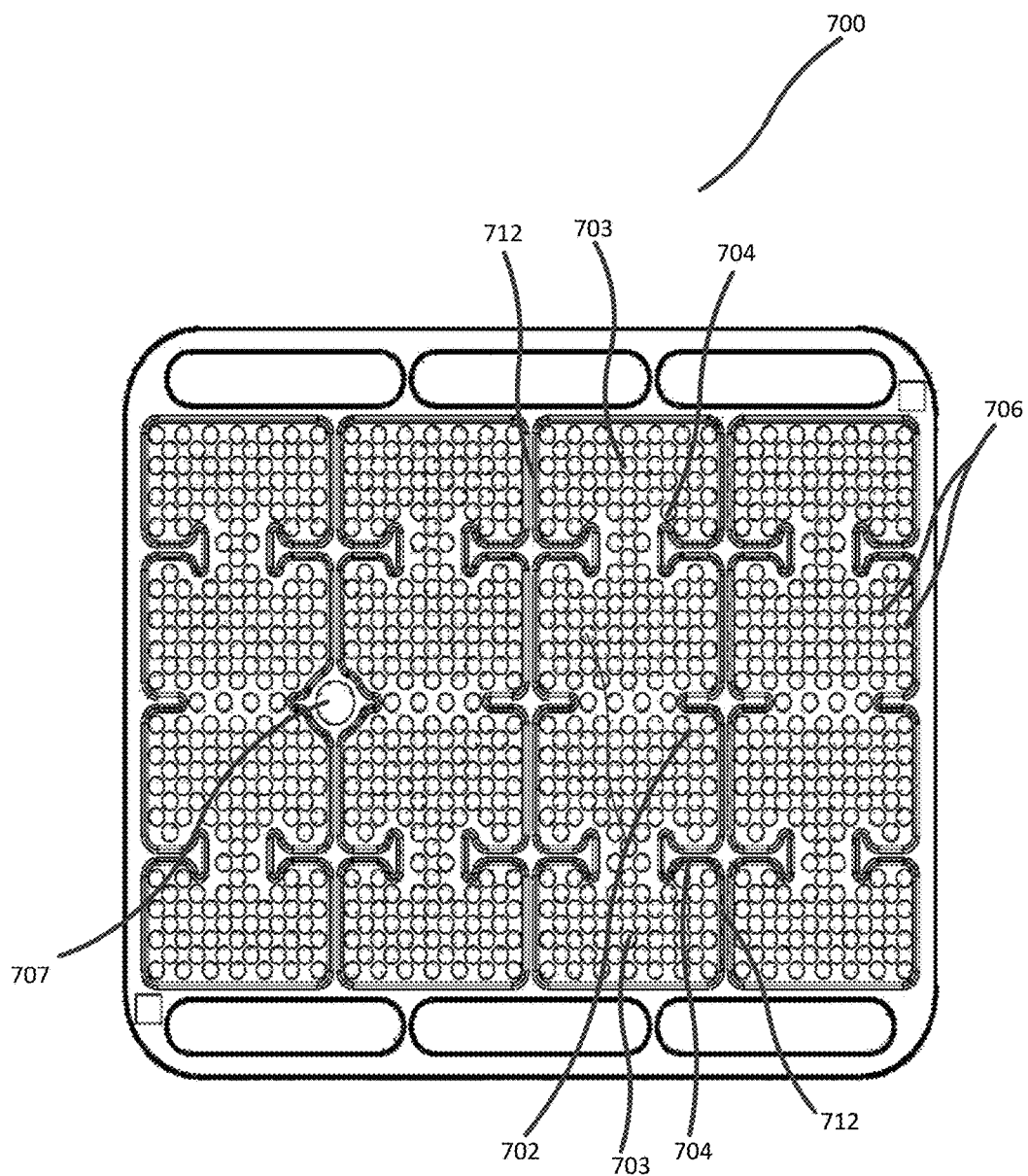
FIG. 7D is a plan view illustration of a representative embodiment of a tray for use in a continuous system described herein.

In an exemplary tray embodiment of FIG. 7A, eight workpieces (including, for example 708, 709, 710, and 711) in adjacent compartments are isolated from each other by compartment walls 712. The prosthesis is separated from the support material and material blank by, for example, mechanical means to dislodge, loosen or pry the prosthesis from the support material, or by a fluid to melt or dissolve the support material. When separated, the plurality of custom prostheses remain separated by compartment walls 712 to facilitate identification. In another embodiment, a tray 700 illustrated in FIG. 7D, comprises a plurality of compartments in which the first compartment area 702 is configured to hold a large workpiece comprising, for example, a multi-unit bridge, for automated and concurrent separation of larger restorations. The enlarged first compartment area is separated by a second compartment area by a wall 712 having an opening into which a portion of the workpiece, e.g. the mandrel 502, is inserted. In the embodiment of FIG. 7D, the tray comprises four compartments in which the orientation of the workpiece within the large first compartment area 702 may be selected, and the mandrel may be inserted through a wall opening leading to one of two adjacent second compartment areas 703.

In either embodiment, a multi-compartment tray that is only partially filled with workpieces may be conveyed through the separation process, for example, to avoid delay. In another embodiment, a tray may comprise a single compartment for holding a single workpiece during the separation process. In this embodiment, multiple trays may be sequentially or simultaneously fed through the automated system by a conveyor, while retaining workpieces in separate trays.

With reference to FIGS. 1A and 1B, and FIGS. 9A through 9C, transfer conveyor 104 transfers tray 108 to the separating unit 102, 900 through an opening 904 in separating tank 901, to engage with the separating unit conveyor 902. The separating unit 900 may comprise a separating tank 901 for housing a separating unit conveyor 902 and separating device 903. Optionally, a scrap disposal unit 103 may also be housed in the separating tank 901.

In one embodiment, the separating device 903 comprises a fluid dispensing device that dispenses a fluid to liquefy the support material, separating the prosthetic from the material block. Where the support material is a wax, the separating device may comprise a dewaxer 1000 (FIGS. 10A-10E) that distributes, for example, hot water or steam, to melt a wax support material 507 and dislodge the prosthesis 504. In this embodiment, the separating tank 901 comprises a stainless steel sink which holds the water generated by the separating device. The tank also serves as a frame to support parallel ribs 907 that support guide rails and pulleys of the separating unit conveyor 902 within the tank.

In one embodiment, the separating unit conveyor 902 comprises two parallel conveyor belts 908 that are spaced compatibly with tray 108 dimensions to allow water and wax to flow through the tray and between the parallel belts 908, and for the disposal of remnant material blanks through an opening 910 in the tank. The parallel conveyor belts may have teeth on one side for engagement with a sprocket of a pulley system 911; alternatively, conveyor belts may be double sided, also having teeth on a second side for engagement with the tray. Movement of the tray may be calculated based on the increment of belt teeth needed to bring the tray in alignment with the separating component. A common pulley drive may be shared by both belts insuring synchronization, and tension may be adjusted by two tensioning idlers. A driving shaft 912 may comprise a rotary seal and two bearing inserts to compensate for any misalignment.

Separating unit 900 and tank 901 may be comprised stainless steel or high temperature plastic for durability from heat and water. Shafts supported from the outside of the tank may comprise seals to insure water retention. The separating 901 tank may further comprise a sensor to detect the level of water inside the tank. A transparent lid 913 may further be provided for viewing within the tank.

A dewaxer 1000 is exemplified that comprises a manifold 1001 connected to an inlet port 1002 through which fluid is introduced to passages in the manifold 1001. In one embodiment, the manifold comprises a network of pipes, channels or tubes that split into multiple dispensing openings 1004 to deliver fluid to the tray. The fluid may comprise for example, hot air, steam or liquid, such as hot water having a temperature greater than the melt temperature of the support material. In one embodiment, the fluid comprises hot water heated to about 100° C. by a heater connected to the separating unit.

Figure 10A:
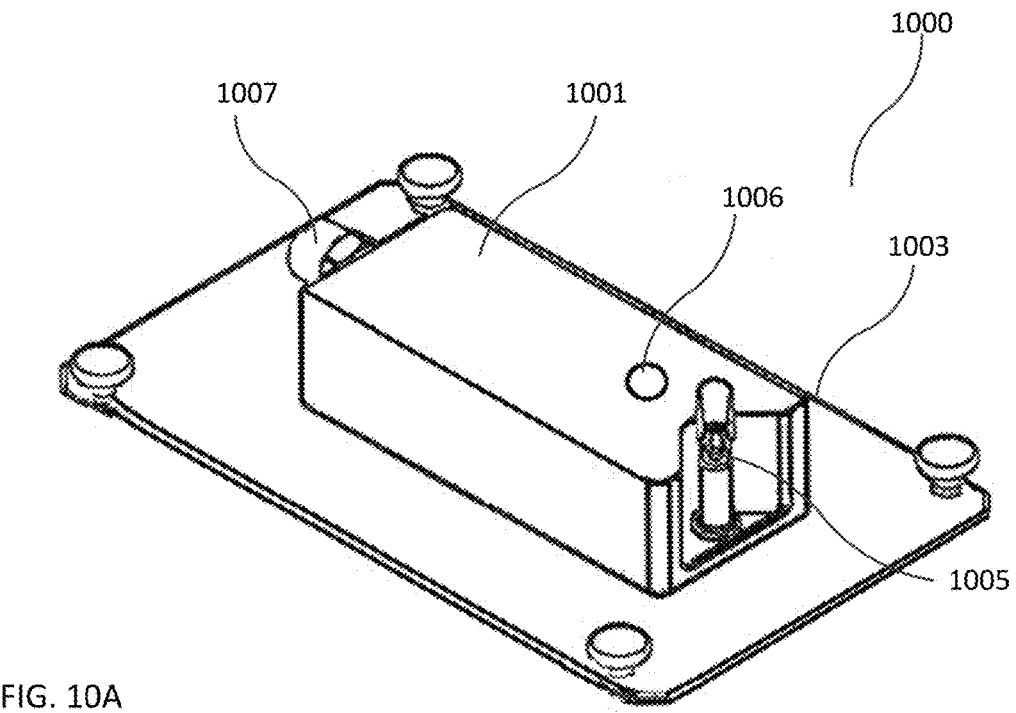
FIG. 10A is an illustration of a perspective view of a separating device according to one embodiment described herein.
Figure 10B:
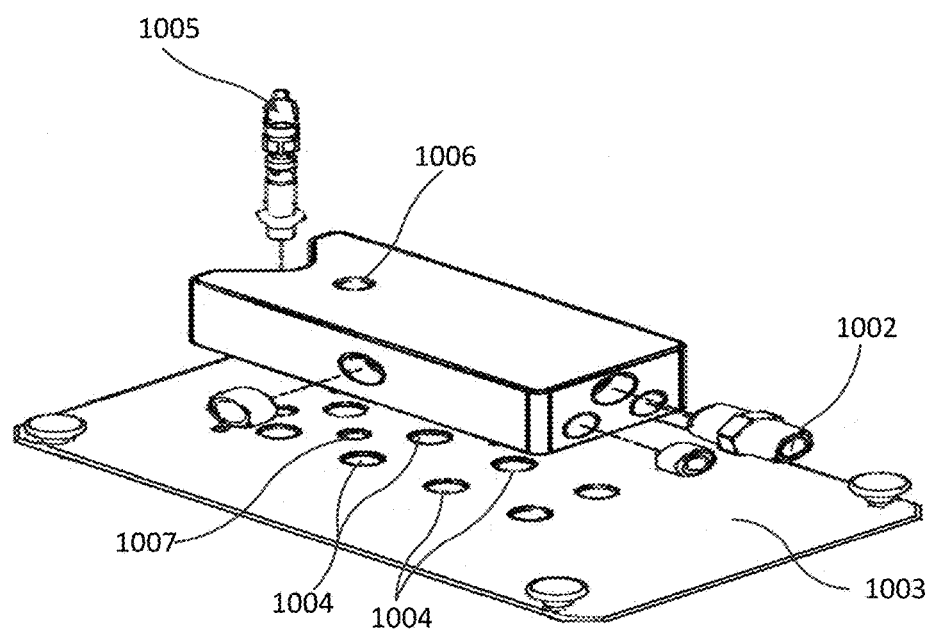
FIG. 10B is an illustration of an exploded view of a separating device according to one embodiment described herein.
Figure 10C:
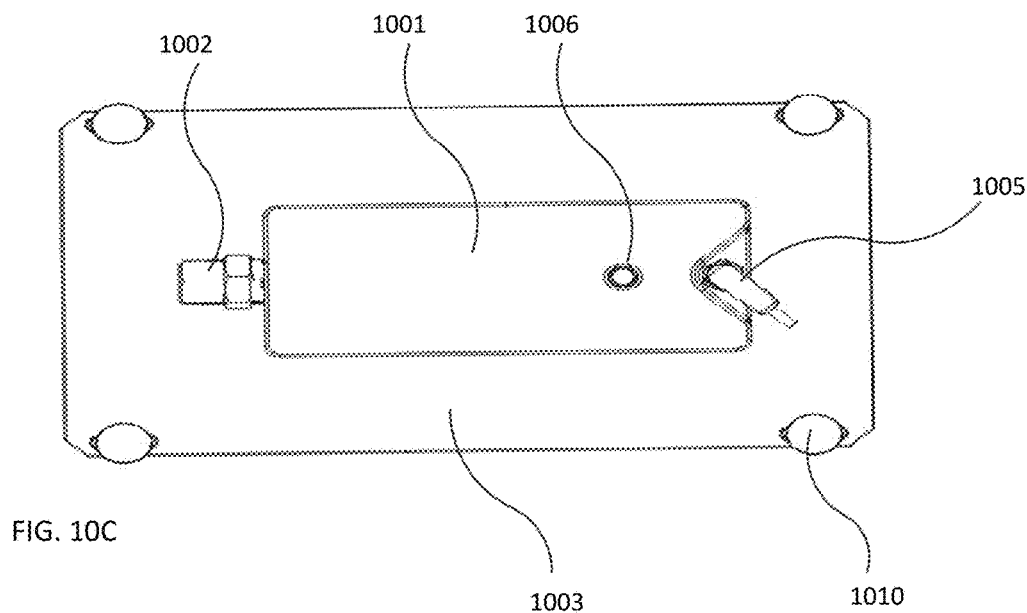
FIG. 10C is an illustration of a plan view of a separating device according to one embodiment described herein.
Figure 10D:
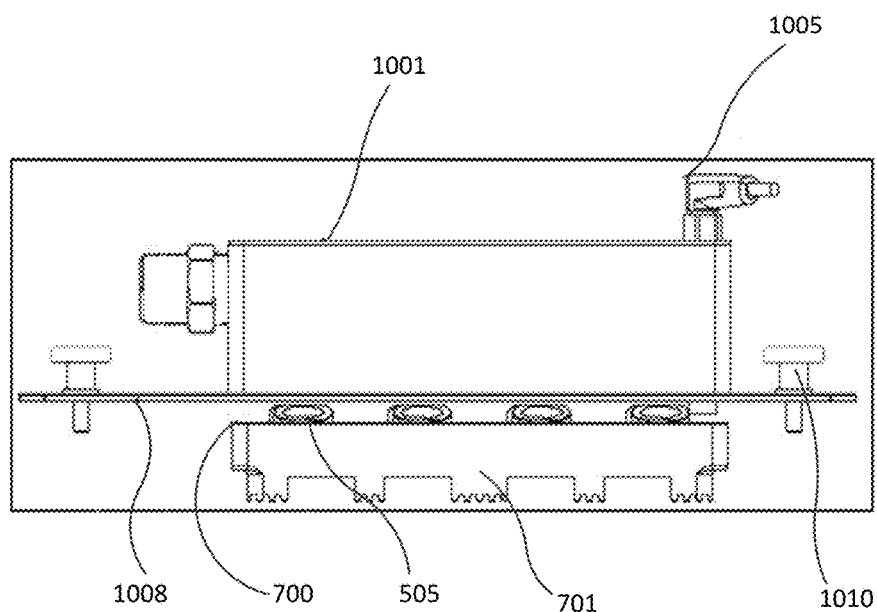
FIG. 10D is an illustration of a side view of a separating device and a tray comprising workpieces according to one embodiment described herein.
Figure 10E:
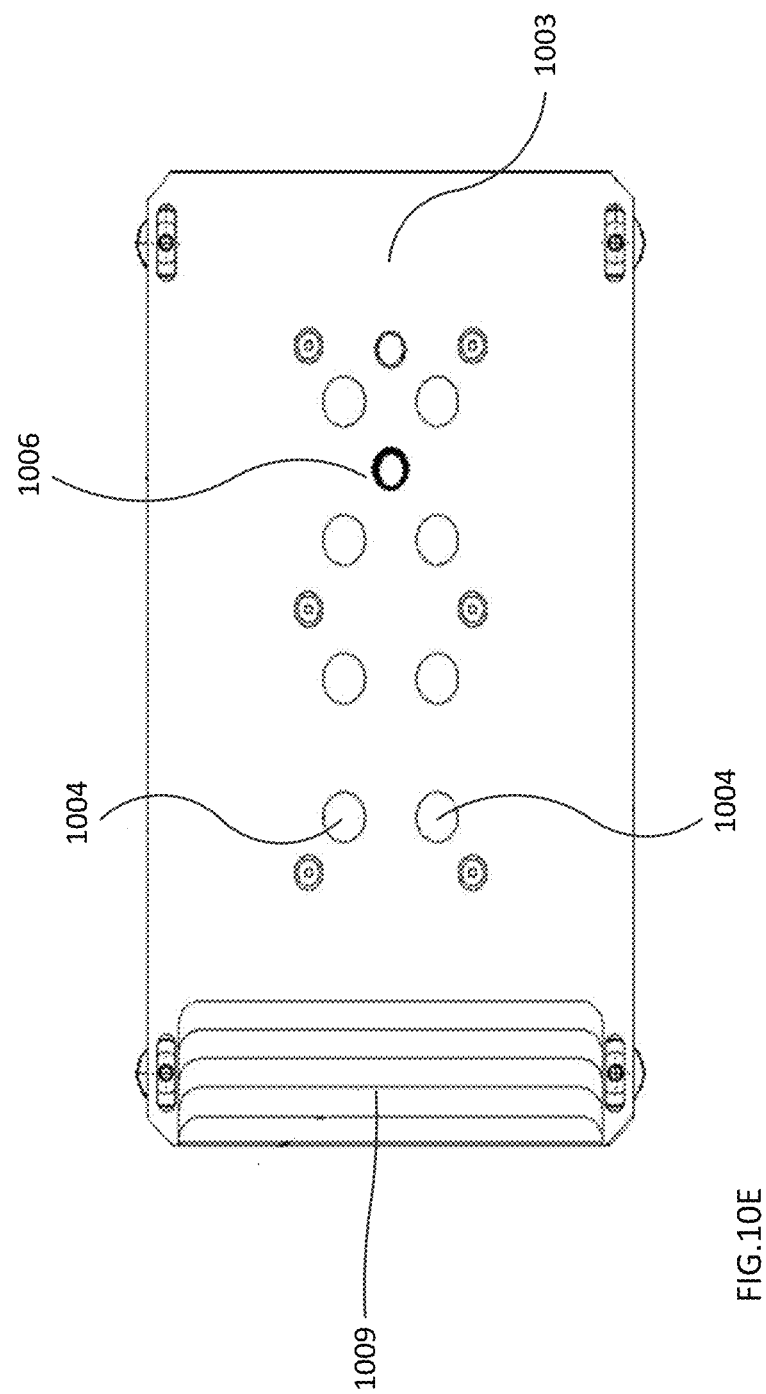
FIG. 10E is an illustration of a bottom view of a manifold plate of a separating device according to one embodiment described herein.

A manifold plate 1003 may be provided that is integral with, or attached to, the manifold 1001. The plate 1003 overlays a tray 700 that has been conveyed into position for the separating process, as illustrated in FIG. 10D. Optionally, the plate rests on rails to provide a gap between the bottom surface 1008 of the manifold and the top of the tray walls 712. A plurality of dispensing openings 1004 in the manifold and/or manifold plate 1003 align with the tray first compartment areas 702 and distribute fluid directly on the support material 505 of the workpieces held therein. In one embodiment, each tray compartment is aligned with a manifold dispensing opening 1004 that has a diameter that is approximately equal to the width of the mill block; in one specific embodiment, a manifold dispensing opening 1004 has a diameter that is approximately ¾".

As fluid is dispensed and support material is liquefied, the manifold plate retains the prostheses within the individual tray compartments upon release from the support material. Optionally, the gap formed between the top of the tray walls 712 and the manifold plate is adjustable by knobs 1010, and the gap is selected to be less than the smallest dimension of the prostheses contained therein.

A sensor 1005 may be provided to detect the tray within the separating unit, sending a signal to begin the separating process, for example, by signaling a pump to dispense hot water. Optionally, a set of alignment holes (1006, 1007, 707) confirms alignment of tray compartments with dispensing openings. An indicator hole in each of the manifold (at 1006), manifold plate (at 1007), and tray (at 707), vertically align when the dispensing holes (1104) of the manifold plate are vertically aligned with the support material 505 within compartments of the tray. A manifold plate lower surface 1008 may further comprise one or more blades 1009 for reducing the volume support material from workpieces 505 that extends higher than the lower surface of the manifold plate 1008. When the tray is conveyed into position below the manifold plate 1008, excess support material may be skimmed by the blade 1009 reducing the level and amount of support material to be removed during the separation process.

A tray 700 comprises a plurality of small drain holes 706 through which liquefied support material and/or fluid from the separation process may flow out of the tray, and, for example, into the separating tank 901. Tray drain holes, smaller than the prostheses, are sized to retain prostheses within the tray upon removal of the support material. The number and size of drain holes 706 may be calculated to provide a fluid/support material removal rate that is greater than the rate at which a volume of fluid is introduced through the manifold to each tray compartment. The separating unit tank 901 may be modified to accommodate greater or lesser amounts of fluid, such as water. The tray may comprise tray feet 701 to elevate the tray above the conveyor, and to allow drainage of fluid and melted wax through the tray bottom.

Trays may grip conveyor belts via friction, or trays may also comprise tray feet optionally having teeth 705 that grip or grab wet surface of the conveyor belt to maintain position of the tray within the system. Parallel, spaced conveyor belts allow fluid and support material to flow through tray drain holes in tray compartments, between the belts and into the separating tank 901. Fluid and wax may be removed from the tank 901 by a tank drain hole 906 leading to pipes or tubing, and optionally recycled in a recycling unit. Fluid may also facilitate cleaning the prostheses, for example, by removing powder or dust from surfaces left after the machining process.

In one embodiment, after removing the support material from the workpieces, the tray is conveyed to a scrap removal station 103 for automatic removal of remnant dental material block after separation from the prosthetic by the separating unit 102. A scrap disposal unit 103, exemplified in the exploded view of FIG. 11A, and in FIGS. 11B, 11C, and 11D, may be contained within the separating tank 901 next to the separating unit 102. In one embodiment, the scrap disposal unit may comprise a scrap disposal device, a removal conveyor, and a sensor for detecting the alignment of the tray with the scrap disposal device. Optionally, a scrap receptacle 909 for holding the scrap remnant blocks and a chute 910 may be provided. A scrap disposal device 1100 may comprises a plurality of gripping devices 1101 attached to a gripper plate 1103, and a vertical actuator 1102 moves the gripper plate up and down. In one embodiment, where the scrap disposal unit is contained within the separating tank 901 with the separating unit 102, the separating conveyor conveys the tray to both the separating unit and the scrap disposal unit illustrated in FIGS. 9B and 9C.

Figure 11A:
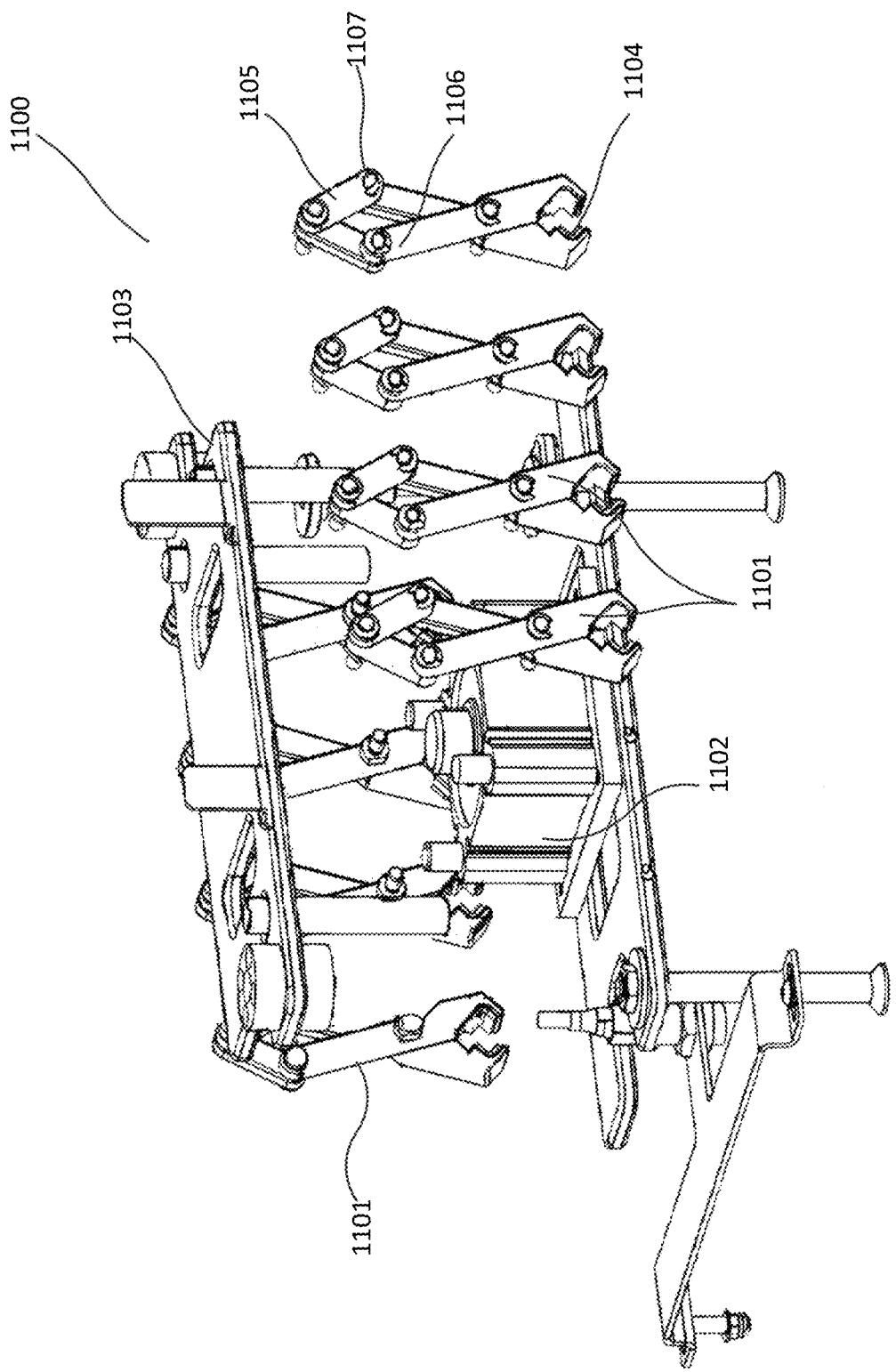
FIG. 11A is an illustration of an exploded view of one embodiment of a component of the scrap disposal unit of the continuous system described herein.

In FIG. 11A, a portion of the scrap disposal device 1100 is shown in exploded format. In this embodiment, eight gripping devices 1101 are shown, four of which are shown disassembled from the gripper plate 1103, for illustrative purposes. The number of gripping devices may vary, depending for example, on the number of compartments in the trays used in the system, or the number of workpieces that can be accommodated by separating unit. The gripping devices are in spaced arrangement corresponding to the spacing of the workpieces as they are conveyed through the scrap disposal unit. In one embodiment, each gripping device in the scrap disposal unit is in a corresponding spaced arrangement with the second compartment areas of the tray compartments.

The gripping mechanism may comprise a two-fingered gripping device 1101 having gripper ends 1104 configured to grip, for example, a portion of the shaped mandrel 502 to lift and remove the remnant block from the tray. In one embodiment, the gripping device 1101 comprises external gripper ends 1104 in scissor-like configuration to grip the external surface of a remnant material block. The ends of the two-finger grippers 1104 may comprise pads, such as silicone pads, to facilitate gripping.

Figure 11B:
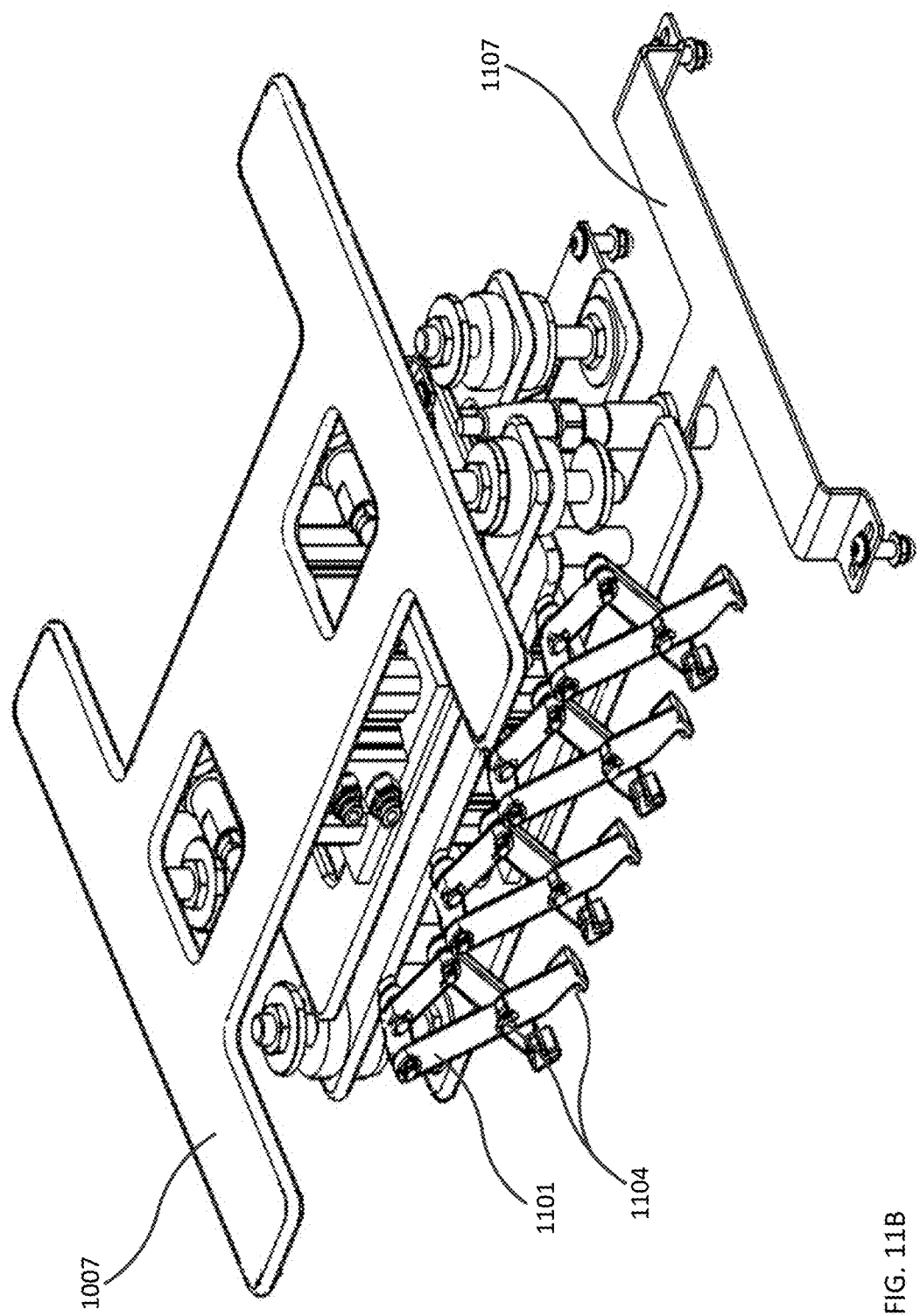
FIG. 11B is a partially exploded view of one embodiment of a component of the scrap disposal unit of the continuous system described herein.
Figure 11C:
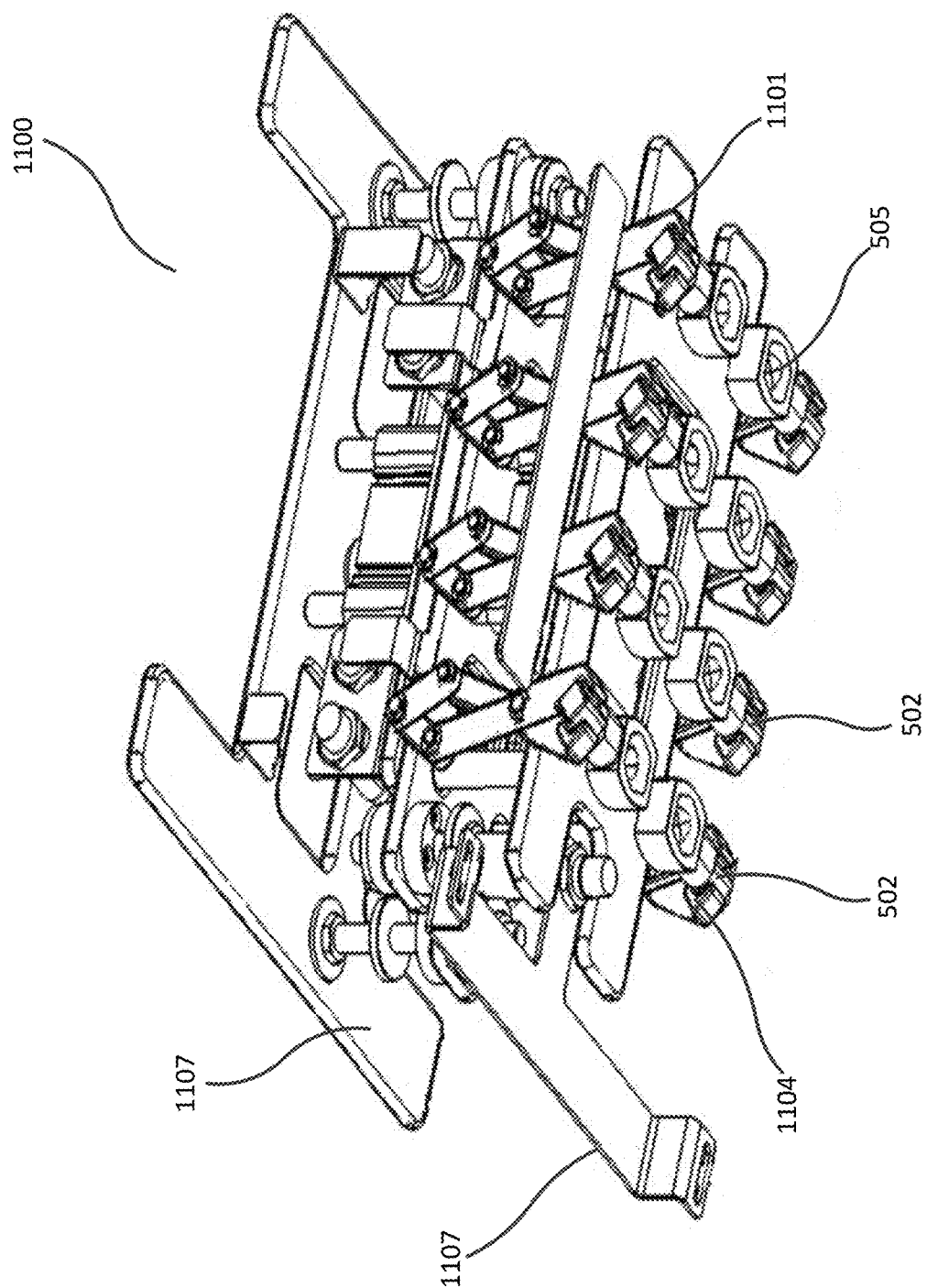
FIG. 11C is a perspective view of the bottom of one embodiment of a component of the scrap disposal unit of the continuous system described herein, and a plurality of remnant material blocks.
Figure 11D:
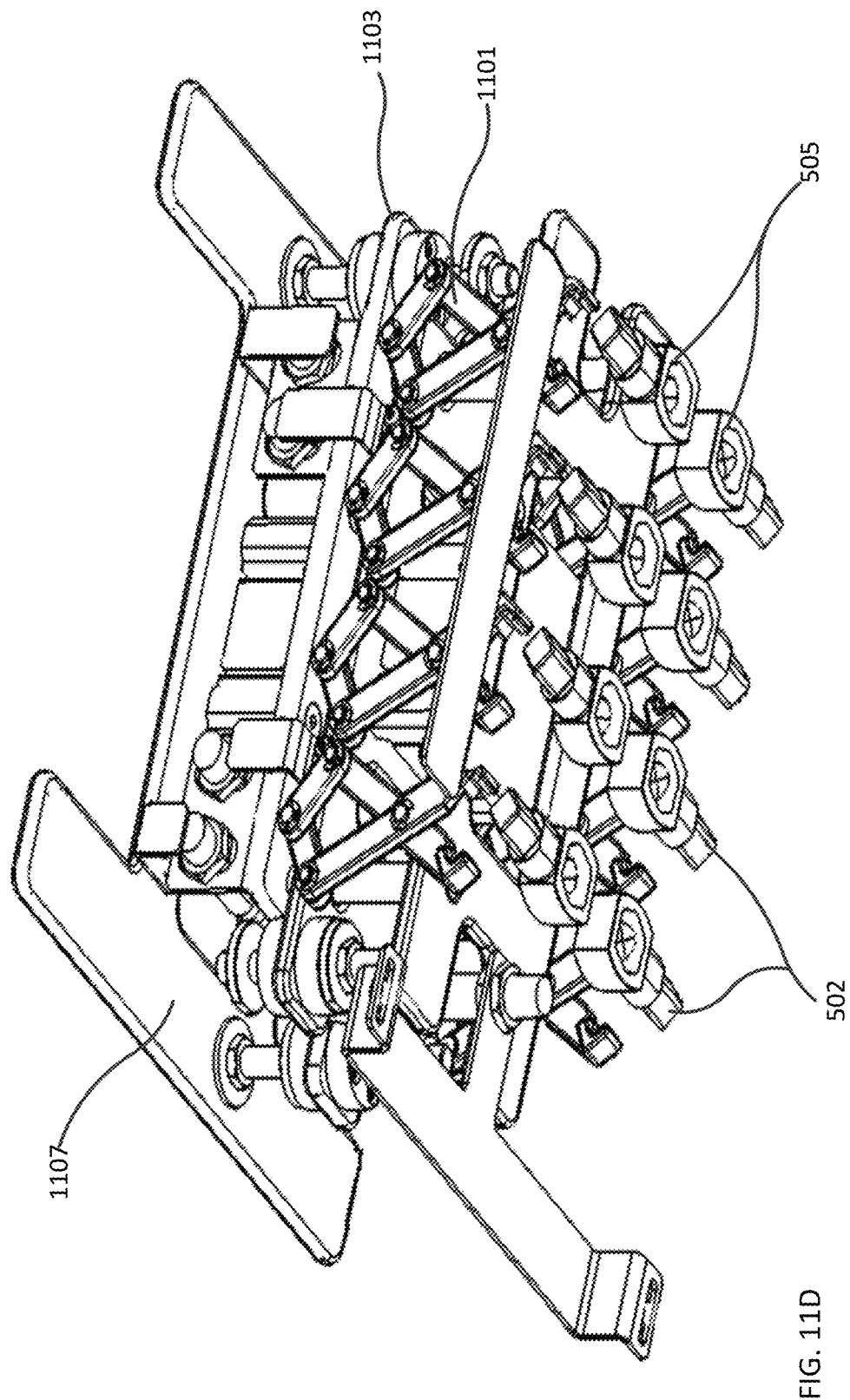
FIG. 11D is a perspective view of the bottom of one embodiment of a component of the scrap disposal unit of the continuous system described herein, and a plurality of remnant material blocks.

Gripper plate 1103 may be connected to a portion of a scrap disposal frame 1107 that supports the scrap disposal device 1100 with the separating tank. The gripper plate 1103 may be lifted or lowered, for example by activation of a cylinder to cause movement of links 1105 thereby moving cantilevered shafts 1106 connected to the links 1105 by joints 1107. The gripper ends are opened as the gripping plate and gripping devices are lowered (FIGS. 11B and 11D). The lowered, open gripper ends fit within compartments of a tray that has been conveyed and positioned in alignment with gripping devices of the scrap disposal device. Upon lifting the gripper plate 1103, the gripper ends 1104 close around a portion of the mandrels 502 of workpieces that are positioned within compartments of a tray. The gripping devices 1101 are lifted, simultaneously lifting and removing a plurality of remnant material blocks 505 from the tray compartments (FIG. 11C). Each prosthesis remains in the individually identified tray compartment, completely separated from the remnant material block 505. In this embodiment, the gripping device is configured so that the gripper ends fit within the individual tray compartment in both the open and closed position to open and close around the remnant block. In other embodiments, the scissor-like gripping device may be replaced by a vacuum activated devise that is used to remove the remnant material block from the tray and away from the milled prostheses.

In one embodiment, an automated, batch process for simultaneously or concurrently separating a plurality of custom prostheses from remnant material block is provided that comprises the steps of transferring a plurality of workpieces into a plurality of individual compartments of a tray, wherein the workpieces each comprise a patient specific, custom milled prosthesis supported in a remnant material block by a support material; separating each prostheses from the support material and removing the remnant block; and retaining the separated prostheses within individual tray compartments. In one embodiment, the process of separating the prosthesis and the support material comprises dispensing a volume of fluid through a plurality of manifold dispensing openings into the plurality of tray compartments; liquefying the support material and releasing each prostheses from the support material. The method may further comprise a process step for separating the plurality of custom prostheses from the remnant material block by removing the remnant material block from the tray, and retaining the separated prostheses within individual tray compartments for identification.

The tray and separated prostheses, optionally, may be conveyed to an annealing or heat treatment station 105 via an oven conveyor 106. In some embodiments where residue from support material remains on the prostheses after separation, the automated process further comprises in a heat treatment station 105 to remove residual support material. In one embodiment, the heat treatment station comprises a conveyor oven heated to a temperature above the boiling temperature of the support material, and comprises an oven conveyor belt for moving trays containing prostheses through the oven. Commercially available conveyor ovens are suitable for use herein provided they can heat the prostheses to a temperature sufficient for eliminating the residual support material. In one embodiment, where the support material comprises a paraffin wax having a boiling temperature of about 370° C., the prostheses contained within compartments of a tray are conveyed on an oven conveyor 106 through a heated oven, for example for a conveying time of about 10 minutes. The oven temperature setting may be between about 550° C., or the oven may be heated to a temperature at which residual support material, such as wax is removed, for example by boiling. The conveyor speed and oven temperature may be optimized to ensure sufficient heating of the prostheses occurs to remove any residual support material. In another embodiment, an enclosed oven may be heated to a temperature between about 400 to 600° C., and the prostheses are heated for a time sufficient to insure removal of any residual wax.

In one embodiment, a tray is designed to withstand the high temperature of a heat treatment station, and provide adequate heat to the prostheses to ensure residual support material is removed. As heat is lost to the tray while conveyed through the heat treatment station, the prostheses may be inadequately heated to remove residual support material resulting in discoloration in final restorations. A tray is described herein having a sufficient heat capacity to the prostheses to remove residual support material. In a further embodiment, a tray is designed having low heat capacity to heat quickly and maintain the overall speed of the automated system. In one embodiment, a stainless steel tray may be designed that comprises sufficient durability to heat and water for use in the separation processes described herein. Stainless steel (e.g., 304 SS, specific heat capacity of about 29.8 cal/lb-° F.) has a lower heat capacity than aluminum (e.g. 6061-T6 specific heat capacity of about 53.5 cal/lb-° F.). The higher density of stainless steel results in a tray having a greater weight than an aluminum tray of the same dimensions, and therefore, overall greater specific heat capacity for a given tray design. A stainless steel tray may require more heat to adequately heat prostheses and remove residual support material. In another embodiment, an aluminum tray may be designed that comprises sufficient durability to both heat and water exposure for use in the separation processes described herein, and also comprises a low specific heat capacity for use in the residual support removal process described herein. In one embodiment, an aluminum tray is provided as illustrated in FIGS. 7A, 7B, 7C, and 7D, having compartments for about eight prostheses, and having a weight of less than about one pound and an overall tray heat capacity of less than about 53 calories. A similarly sized stainless steel tray comprising a plurality of compartments for holding about eight prostheses may comprise a weight of greater than 2.75 lbs. (pounds), and therefore have an overall heat capacity greater than about 80 calories.

In a further embodiment, a tray is provided that is comprised of a material having a similar coefficient of thermal expansion as the prostheses held therein during a heat treatment process. Trays made from materials having dissimilar coefficients of thermal expansion as the prostheses may result in chipping and cracking during heat-requiring stations of the automated process. Tray materials may further require sufficient strength and oxidation resistance to withstand repeated use in the disclosed automated system. Thus, a tray is provided having an overall heat capacity value to remove residual support material from prostheses, and a substantially similar coefficient of thermal expansion as the prostheses material to avoid chipping and/or cracking. In one embodiment, a tray is comprised of a metal that is harder than the restoration; trays comprising a metal that is softer than the restoration may result in visible markings on the restoration. In an embodiment where aluminum is softer than the machined restoration, a tray is provided that comprises a hard anodized aluminum that is sufficiently hard to prevent markings on the restoration, has sufficiently low heat capacity to heat the restoration to remove any residual support material, and comprises resistance to corrosion from heat and water through an automated system.

Figure 12:
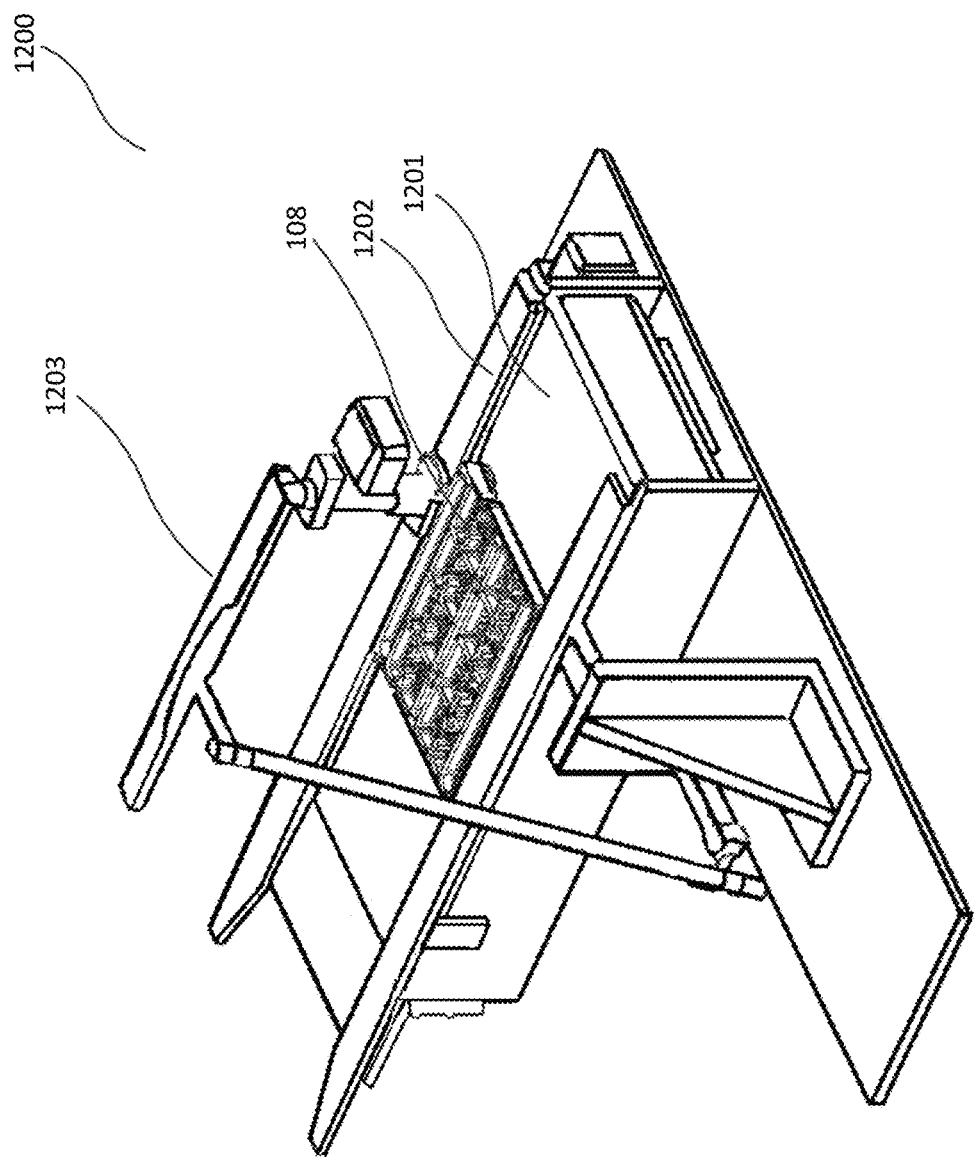
FIG. 12 is an illustration of one embodiment of a cooling unit of the continuous system described herein.

An optional cooling station 1200 may be provided as exemplified in FIG. 12. Trays 108 comprising restorations heated in an oven 105 may be conveyed between parallel guide rails 1202 from the conveyor oven 105 to a cooling conveyor 1201. A cooling device 1203, such as an air knife, may be used to cool the prostheses and tray. After cooling, the custom prostheses may be removed from individual tray compartments for further processing according to the custom dental prosthesis information stored, for example, in a dental prosthesis database. Further processes may comprise staining, glazing and/or sintering.

A kit is provided for making a plurality of patient-specific dental restorations that comprises a multi-compartment tray and a plurality of material blocks. The tray comprises a plurality of compartments each having first and second compartment areas for holding the material blocks. The material blocks comprise a material portion for shaping the custom dental restoration, and the material portion comprises upper and lower milling surfaces that are accessible by the milling tool for milling the dental restorations. The upper and lower surfaces are joined by two side surfaces that may be optionally curved (FIG. 5A), and opposing top and bottom surfaces. The material portion fits within the first compartment area of the tray. The material blocks each comprise a mandrel for securing in the mill unit and transferring into and out of the tray. Optionally, the mandrel fits through an opening in a wall separating the first and second compartment areas. The mandrel comprises a first elongated portion having a first end that is attached to the bottom surface of the material block portion and an opposing second end comprising a shoulder. The second elongated portion is adjacent the first elongated portion at a second end of the first elongated portion. The second elongated portion optionally, has a cross-sectional geometry that is smaller than the first elongated portion for the length of the second portion. Optionally, the first elongated portion ends at the shoulder which extends beyond the exterior geometry of the second elongated portion. The first elongated portion optionally, comprises at least one planar surface, or optionally, two opposing planar surfaces. The second elongated portion has at least one flat surface that is not orthogonal to a planar surface of the first elongated portion. Optionally, the second elongated portion as two adjacent planar surfaces, and optionally, the two adjacent planar surfaces are not orthogonal the flat surfaces of the first elongated portion.

The custom dental prosthesis information can be provided to the dental prosthesis management system as dental prosthesis information and stored as an entry in a dental prosthesis database. The dental prosthesis information can include such information as the type of dental prosthesis to be manufactured (e.g., crowns, implants, bridges, and the like etc.), a material type from which the dental prosthesis is to be manufactured, an identification of the tooth or portion of a tooth to be prosthetically recreated, and situational data concerning the position of the dental prosthesis in a patient's mouth (e.g., data concerning a dental impression, or photographic data). In addition, the dental prosthesis information can include the design information created for the design of the dental prosthesis to be manufactured, such as design information created using a dental CAD software program. Optionally, the dental prosthesis information may also include identification information concerning a dentist or dental office requesting manufacture of the dental prosthesis, and/or patient identification information. A generalized example of a suitable computing environment in which the described innovations may be implemented is described. The computing environment is not intended to suggest any limitation as to scope of use or functionality, as the innovations may be implemented in diverse general-purpose or special-purpose computing systems. For example, the computing environment can be any of a variety of computing devices (e.g., desktop computer, laptop computer, server computer, tablet computer, gaming system, mobile device, programmable automation controller, etc.) that can be incorporated into a computing system comprising one or more computing devices. A computing environment may include one or more processing units and memory. Processing units execute computer-executable instructions, and a processing unit can be a central processing unit (CPU), a processor in an application-specific integrated circuit (ASIC), or any other type of processor. A central processing unit as well as a graphics processing unit or co-processing unit may be provided. The tangible memory may be volatile memory (e.g., registers, cache, RAM), non-volatile memory (e.g., ROM, EEPROM, flash memory, etc.), or some combination of the two, accessible by the processing unit(s). The memory stores software implementing one or more innovations described herein, in the form of computer-executable instructions suitable for execution by the processing unit(s).

A computing system may have additional features. For example, in some embodiments, the computing environment includes storage, one or more input devices, one or more output devices, and one or more communication connections. An interconnection mechanism (not shown) such as a bus, controller, or network, interconnects the components of the computing environment. Typically, operating system software (not shown) provides an operating environment for other software executing in the computing environment, and coordinates activities of the components of the computing environment.

Tangible storage may be removable or non-removable, and includes magnetic or optical media such as magnetic disks, magnetic tapes or cassettes, CD-ROMs, DVDs, or any other medium that can be used to store information in a non-transitory way and can be accessed within the computing environment. Storage stores instructions for software implementing one or more innovations described herein.

An input device(s) may be, for example: a touch input device, such as a keyboard, mouse, pen, or trackball; a voice input device; a scanning device; any of various sensors; another device that provides input to the computing environment; or combinations thereof. For video encoding, the input device(s) may be a camera, video card, TV tuner card, or similar device that accepts video input in analog or digital form, or a CD-ROM or CD-RW that reads video samples into the computing environment. The output device(s) may be a display, printer, speaker, CD-writer, or another device that provides output from the computing environment.

Communication connection(s) enable communication over a communication medium to another computing entity. The communication medium conveys information, such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

In some embodiments disclosed methods may be implemented as computer-executable instructions stored on one or more computer-readable storage media (e.g., one or more optical media discs, volatile memory components (such as DRAM or SRAM), or nonvolatile memory components (such as flash memory or hard drives)) and executed on a computer (e.g., any commercially available computer, including smart phones, other mobile devices that include computing hardware, or programmable automation controllers) (e.g., the computer-executable instructions cause one or more processors of a computer system to perform the method). The term computer-readable storage media does not include communication connections, such as signals and carrier waves. Computer-executable instructions described herein for implementing the disclosed techniques as well as any data created and used during implementation of the disclosed embodiments may be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that functionality described herein may be performed, at least in part, by one or more hardware logic components, instead of software. For example, and without limitation, illustrative types of hardware logic components that may be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) may be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

We claim:

1. A method for processing a plurality of customized, patient-specific dental restorations, comprising
   a. forming a plurality of workpieces from a plurality of individual millable, material blocks to make the plurality of patient-specific dental restorations wherein forming each workpiece comprises
      i. for each customized, patient-specific dental restoration, obtaining an individual, millable, material block from the plurality of millable, material blocks and a computerized dental restoration design designed for a patient;
      ii. shaping a first portion of a dental restoration from the material block according to a first set of machining instructions corresponding to the computerized dental restoration design, and forming a recess within the material block by removing a portion of material block during shaping;
      iii. adding a volume of support material within the recess of the material block formed by shaping the first portion; and
      iv. shaping a second portion of the dental restoration from the material block according to a second set of machining instructions that corresponds to the computerized dental restoration design,
   wherein each workpiece comprises a remnant of the individual material block, the dental restoration and the support material, wherein the dental restoration is supported by the support material within the recess of the workpiece;
   b. transferring each workpiece into a compartment of a multi-compartment tray; and
   c. within the tray, removing the support material from each workpiece within the tray and separating the remnants of the material blocks from the plurality of patient-specific dental restorations.

2. The method of claim 1, wherein the method comprises holding each dental restoration in a separate compartment of the multi-compartment tray after separating the dental restoration from the remnant.

3. The method of claim 1, wherein each compartment of the multi-compartment tray comprises a first compartment area for holding the material block that comprises a plurality of drain holes for removing the support material from the tray and separating the dental restoration from the remnant of the material block.

4. The method of claim 1, wherein the millable, material block comprises a millable zirconia ceramic material.

5. The method of claim 1, wherein the support material comprises a thermoplastic material.

6. The method of claim 1, further comprising the step of determining the volume of support material added to each workpiece based on the geometry of the patient-specific dental restoration.

7. The method of claim 1, further comprising calculating the volume of material block removed to shape the first portion of the dental restoration and determining the volume of support material based on the volume of material block removed.

8. The method of claim 1, wherein the step of removing the support material comprises liquefying the volume of support material in the plurality of workpieces within the multi-compartment tray.

9. The method of claim 1, wherein the tray comprises a plurality of drain holes.

10. The method of claim 1, wherein the tray is comprised of anodized aluminum.

11. The method of claim 1, wherein the tray comprises an overall heat capacity of less than 53 calories.

12. A method for processing a plurality of customized, patient-specific dental restorations, comprising
   a. forming a plurality of workpieces to make the plurality of patient-specific dental restorations wherein forming each workpiece comprises
      i. obtaining a millable, material block and a computerized dental restoration design designed for a patient;
      ii. shaping a first portion of a dental restoration from the material block according to a first set of machining instructions corresponding to the computerized dental restoration design, and forming a recess within the material block by removing a portion of material block during shaping;
      iii. adding a volume of support material within the recess of the material block formed by shaping the first portion; and
      iv. shaping a second portion of the dental restoration from the material block according to a second set of machining instructions that corresponds to the computerized dental restoration design,
      wherein each workpiece comprises a remnant of the material block, the dental restoration and the support material, wherein the dental restoration is supported by the support material within the recess of the workpiece;
   b. transferring each workpiece into a compartment of a multi-compartment tray,
      wherein each compartment of the multi-compartment tray comprises first and second compartment areas, and transferring comprises aligning the first portion of the material block for shaping the dental restoration within the first compartment area, and aligning a mandrel connected to the first portion of the material block within a second compartment area,
      wherein the first compartment area and the second compartment area are separated by a wall having an opening and the mandrel fits within the wall opening;
   c removing the support material from each workpiece within the tray; and
   d. separating the remnants of the material blocks from the plurality of patient-specific dental restorations.

13. A method for forming a plurality of workpieces from a plurality of millable blocks to make a plurality of patient-specific dental restorations, comprising:
   a. for each workpiece, obtaining a millable, material block from the plurality of millable blocks and obtaining machining instructions for shaping a computerized dental restoration design designed for a patient and for dispensing a volume of a liquid support material specific to the dental restoration design;
   b. forming each workpiece within a milling system, comprising
      i. shaping a first portion of a dental restoration from the material block corresponding to the computerized dental restoration design, and forming a recess within the material block by removing a portion of material block during shaping in a milling unit;
      ii. dispensing the volume of the liquid support material within the recess of the material block-that is in a milling unit;
      iii. allowing at least a portion of the liquid support material to harden to form a hardened support material; and
      iv. shaping a second portion of the dental restoration from the material block corresponding to the computerized dental restoration design,
      wherein each workpiece comprises a remnant of the material block, the dental restoration and the hardened support material,
      wherein the dental restoration is supported by the hardened support material within the recess of the workpiece; and
   c. for each workpiece, separating the dental restoration from the remnant by melting the hardened support material with a hot liquid having a temperature greater than a melt temperature of the support material.

14. The method of claim 13, comprising heating a wax to form the liquid support material.

15. The method of claim 13, comprising dispensing the volume of liquid support material within the recess by a pneumatic dispenser.

16. The method of claim 13, wherein dispensing comprises injecting the volume of liquid support material within the recess by a dispenser utilizing pressurized air.

17. The method of claim 13, further comprising dispensing cold air within the milling unit to harden the liquid support material within the recess.

18. The method of claim 13, wherein, prior to melting the support material, the method comprises transferring each workpiece to a hard anodized aluminum tray having drain holes for removing the melted support material and the hot liquid from the tray.

19. The method of claim 13, further comprising heating a support material to form the liquid support material and delivering the liquid support material to the milling unit.

20. The method of claim 19, comprising utilizing a hot melt system to heat the support material.

* * * * *